(12) United States Patent
Fink et al.

(10) Patent No.: US 8,196,573 B2
(45) Date of Patent: Jun. 12, 2012

(54) METHODS AND SYSTEMS FOR OPERATING AN AEROSOL GENERATOR

(75) Inventors: James B. Fink, San Mateo, CA (US); John Power, Moycullen (IE); Ehud Ivri, Newport Beach, CA (US); Niall Smith, Alloa (GB); Paul Dunne, Drumcondra (IE); Gavan O'Sullivan, Gort (IE); Declan Moran, Claregalway (IE); Keith Gibbons, Doughiska (IE)

(73) Assignee: Novartis AG, Basel (CH)

( * ) Notice: Subject to any disclaimer, the term of this patent is extended or adjusted under 35 U.S.C. 154(b) by 252 days.

(21) Appl. No.: 12/018,716

(22) Filed: Jan. 23, 2008

(65) Prior Publication Data
US 2008/0142002 A1 Jun. 19, 2008

Related U.S. Application Data

(63) Continuation of application No. 11/090,328, filed on Mar. 24, 2005, which is a continuation-in-part of application No. 10/345,875, filed on Jan. 15, 2003, now Pat. No. 6,968,840, and a continuation-in-part of application No. 10/284,068, filed on Oct. 30, 2002, now Pat. No. 7,600,511, and a continuation-in-part of application No. 09/849,194, filed on May 4, 2001, now Pat. No. 6,615,824, and a continuation-in-part of application No. 09/812,755, filed on Mar. 20, 2001, now Pat. No. 7,100,600.

(60) Provisional application No. 60/381,830, filed on May 20, 2002, provisional application No. 60/344,484, filed on Nov. 1, 2001.

(51) Int. Cl.
A61M 11/00 (2006.01)
A61M 11/06 (2006.01)
A61M 16/10 (2006.01)

(52) U.S. Cl. ......... 128/200.14; 128/200.16; 128/200.21; 128/203.12; 128/204.21; 128/204.26; 239/338

(58) Field of Classification Search ............. 128/200.14, 128/200.21, 200.24, 204.18, 204.26; 239/302, 239/332, 338; 514/34, 37, 39, 41
See application file for complete search history.

(56) References Cited

U.S. PATENT DOCUMENTS
550,315 A 11/1895 Allen
(Continued)

FOREIGN PATENT DOCUMENTS
BE 531640 12/1957
(Continued)

OTHER PUBLICATIONS

Aulton, M.E., "Chapter 20—Therapeutic Aerosols," Pharmaceutics, The Science of Dosage Form Design, pp. 341-358, 1988.

(Continued)

*Primary Examiner* — Clinton T Ostrup
(74) *Attorney, Agent, or Firm* — Kilpatrick Townsend & Stockton LLP

(57) ABSTRACT

A system for intermittent delivery of an aerosolized medicament is disclosed. The system may include an aerosol generator, a controller and a conduit. The aerosol generator may be configured to aerosolize a medicament. The controller may be configured to receive physiological characteristic information about a patient, and control the aerosol generator based at least in part on the physiological characteristic information. The conduit may be configured to supply the aerosolized medicament to the patient's airway.

13 Claims, 21 Drawing Sheets

U.S. PATENT DOCUMENTS

| | | |
|---|---|---|
| 809,159 A | 1/1906 | Willis et al. |
| 1,680,616 A | 8/1928 | Horst |
| 2,022,520 A | 11/1935 | Philbrick |
| 2,101,304 A | 12/1937 | Wright |
| 2,158,615 A | 5/1939 | Wright |
| 2,187,528 A | 1/1940 | Wing |
| 2,223,541 A | 12/1940 | Baker |
| 2,266,706 A | 12/1941 | Fox et al. |
| 2,283,333 A | 5/1942 | Martin |
| 2,292,381 A | 8/1942 | Klagges |
| 2,360,297 A | 10/1944 | Wing |
| 2,375,770 A | 5/1945 | Dahlberg |
| 2,383,098 A | 8/1945 | Wheaton |
| 2,404,063 A | 7/1946 | Healy |
| 2,430,023 A | 11/1947 | Longmaid |
| 2,474,996 A | 7/1949 | Wallis |
| 2,512,004 A | 6/1950 | Wing |
| 2,521,657 A | 9/1950 | Severy |
| 2,681,041 A | 6/1954 | Zodtner et al. |
| 2,693,178 A | 11/1954 | Gilroy |
| 2,705,007 A | 3/1955 | Gerber |
| 2,735,427 A | 2/1956 | Sullivan |
| 2,764,946 A | 10/1956 | Henderson |
| 2,764,979 A | 10/1956 | Henderson |
| 2,779,623 A | 1/1957 | Eisenkraft |
| 2,935,970 A | 5/1960 | Morse et al. |
| 3,066,669 A | 12/1962 | De Melfy |
| 3,083,707 A | 4/1963 | Seeler |
| 3,103,310 A | 9/1963 | Lang |
| 3,247,849 A | 4/1966 | Wise |
| 3,325,031 A | 6/1967 | Singier |
| 3,411,854 A | 11/1968 | Rosler et al. |
| 3,515,348 A | 6/1970 | Coffman et al. |
| 3,530,856 A | 9/1970 | Bird |
| 3,550,864 A | 12/1970 | East |
| 3,558,052 A | 1/1971 | Dunn |
| 3,561,444 A | 2/1971 | Boucher |
| 3,563,415 A | 2/1971 | Ogle |
| 3,680,954 A | 8/1972 | Frank |
| 3,719,328 A | 3/1973 | Hindman |
| 3,738,574 A | 6/1973 | Guntersdorfer et al. |
| 3,771,982 A | 11/1973 | Dobo |
| 3,790,079 A | 2/1974 | Berglund et al. |
| 3,804,329 A | 4/1974 | Martner |
| 3,812,854 A | 5/1974 | Michaels et al. |
| 3,826,413 A | 7/1974 | Warren |
| 3,838,686 A | 10/1974 | Szekely |
| 3,842,833 A | 10/1974 | Ogle |
| 3,858,739 A | 1/1975 | Turner et al. |
| 3,861,386 A | 1/1975 | Harris et al. |
| 3,865,106 A | 2/1975 | Palush |
| 3,903,884 A | 9/1975 | Huston et al. |
| 3,906,950 A | 9/1975 | Cocozza |
| 3,908,654 A | 9/1975 | Lhoest et al. |
| 3,950,760 A | 4/1976 | Rauch et al. |
| 3,951,313 A | 4/1976 | Coniglione |
| 3,958,249 A | 5/1976 | DeMaine et al. |
| 3,970,250 A | 7/1976 | Drews |
| 3,983,740 A | 10/1976 | Danel |
| 3,993,223 A | 11/1976 | Welker, III et al. |
| 4,005,435 A | 1/1977 | Lundquist et al. |
| 4,020,834 A | 5/1977 | Bird |
| 4,030,492 A | 6/1977 | Simburner |
| 4,052,986 A | 10/1977 | Scaife |
| 4,059,384 A | 11/1977 | Holland et al. |
| D246,574 S | 12/1977 | Meierhoefer |
| 4,076,021 A | 2/1978 | Thompson |
| 4,083,368 A | 4/1978 | Freezer |
| 4,094,317 A | 6/1978 | Wasnich |
| 4,101,041 A | 7/1978 | Mauro, Jr. et al. |
| 4,106,503 A | 8/1978 | Rosenthal et al. |
| 4,109,174 A | 8/1978 | Hodgson |
| 4,113,809 A | 9/1978 | Abair et al. |
| D249,958 S | 10/1978 | Meierhoefer |
| 4,119,096 A | 10/1978 | Drews |
| 4,121,583 A | 10/1978 | Chen |
| 4,159,803 A | 7/1979 | Cameto et al. |
| 4,163,450 A | 8/1979 | Kirk et al. |
| 4,207,990 A | 6/1980 | Weiler et al. |
| 4,210,155 A | 7/1980 | Grimes |
| 4,226,236 A | 10/1980 | Genese |
| 4,240,081 A | 12/1980 | Devitt |
| 4,240,417 A | 12/1980 | Holever |
| 4,248,227 A | 2/1981 | Thomas |
| 4,261,512 A | 4/1981 | Zierenberg |
| D259,213 S | 5/1981 | Pagels |
| 4,268,460 A | 5/1981 | Boiarski et al. |
| 4,291,838 A | 9/1981 | Williams |
| 4,294,407 A | 10/1981 | Reichl et al. |
| 4,298,045 A | 11/1981 | Weiler et al. |
| 4,299,784 A | 11/1981 | Hense |
| 4,300,546 A | 11/1981 | Kruber |
| 4,301,093 A | 11/1981 | Eck |
| 4,319,155 A | 3/1982 | Makai et al. |
| 4,334,531 A | 6/1982 | Reichl et al. |
| 4,336,544 A | 6/1982 | Donald et al. |
| 4,338,576 A | 7/1982 | Takahashi et al. |
| 4,368,476 A | 1/1983 | Uehara et al. |
| 4,368,850 A | 1/1983 | Szekely |
| 4,374,707 A | 2/1983 | Pollack |
| 4,389,071 A | 6/1983 | Johnson, Jr. et al. |
| 4,408,719 A | 10/1983 | Last |
| 4,428,802 A | 1/1984 | Kanai et al. |
| 4,431,136 A | 2/1984 | Janner et al. |
| 4,454,877 A | 6/1984 | Miller et al. |
| 4,465,234 A | 8/1984 | Maehara et al. |
| 4,470,412 A | 9/1984 | Nowacki et al. |
| 4,474,251 A | 10/1984 | Johnson, Jr. |
| 4,474,326 A | 10/1984 | Takahashi |
| 4,475,113 A | 10/1984 | Lee et al. |
| 4,479,609 A | 10/1984 | Maeda et al. |
| 4,512,341 A | 4/1985 | Lester |
| 4,530,464 A | 7/1985 | Yamamoto et al. |
| 4,533,082 A | 8/1985 | Maehara et al. |
| 4,539,575 A | 9/1985 | Nilsson |
| 4,544,933 A | 10/1985 | Heinzl |
| 4,546,361 A | 10/1985 | Brescia et al. |
| 4,550,325 A | 10/1985 | Viola |
| 4,566,452 A | 1/1986 | Farr |
| 4,591,883 A | 5/1986 | Isayama |
| 4,593,291 A | 6/1986 | Howkins |
| 4,605,167 A | 8/1986 | Maehara |
| 4,613,326 A | 9/1986 | Szwarc |
| 4,620,201 A | 10/1986 | Heinzl et al. |
| 4,628,890 A | 12/1986 | Freeman |
| 4,632,311 A | 12/1986 | Nakane et al. |
| 4,658,269 A | 4/1987 | Rezanka |
| 4,659,014 A | 4/1987 | Soth et al. |
| 4,677,975 A | 7/1987 | Edgar et al. |
| 4,678,680 A | 7/1987 | Abowitz |
| 4,679,551 A | 7/1987 | Anthony |
| 4,681,264 A | 7/1987 | Johnson, Jr. |
| 4,693,853 A | 9/1987 | Falb et al. |
| 4,702,418 A | 10/1987 | Carter et al. |
| 4,722,906 A | 2/1988 | Guire |
| 4,753,579 A | 6/1988 | Murphy |
| 4,790,479 A | 12/1988 | Matsumoto et al. |
| 4,793,339 A | 12/1988 | Matsumoto et al. |
| 4,796,807 A | 1/1989 | Bendig et al. |
| 4,799,622 A | 1/1989 | Ishikawa et al. |
| 4,805,609 A | 2/1989 | Roberts et al. |
| 4,819,629 A * | 4/1989 | Jonson ............. 128/203.22 |
| 4,819,834 A | 4/1989 | Thiel |
| 4,823,784 A | 4/1989 | Bordoni et al. |
| 4,826,080 A | 5/1989 | Ganser |
| 4,826,759 A | 5/1989 | Guire et al. |
| 4,828,886 A | 5/1989 | Hieber |
| 4,843,445 A | 6/1989 | Stemme |
| 4,849,303 A | 7/1989 | Graham et al. |
| 4,850,534 A | 7/1989 | Takahashi et al. |
| 4,865,006 A | 9/1989 | Nogi et al. |
| 4,871,489 A | 10/1989 | Ketcham |
| 4,872,553 A | 10/1989 | Suzuki et al. |
| 4,877,989 A | 10/1989 | Drews et al. |
| 4,888,516 A | 12/1989 | Daeges et al. |
| 4,922,901 A | 5/1990 | Brooks et al. |
| 4,926,915 A | 5/1990 | Deussen et al. |

| | | | | | | |
|---|---|---|---|---|---|---|
| 4,934,358 A | 6/1990 | Nilsson et al. | 5,378,231 A * | 1/1995 | Johnson et al. | 604/67 |
| 4,954,225 A | 9/1990 | Bakewell | 5,383,906 A | 1/1995 | Burchett et al. | |
| 4,957,239 A | 9/1990 | Tempelman | 5,388,571 A | 2/1995 | Roberts et al. | |
| 4,964,521 A | 10/1990 | Wieland et al. | 5,388,572 A | 2/1995 | Mulhauser et al. | |
| D312,209 S | 11/1990 | Morrow et al. | 5,392,768 A | 2/1995 | Johansson et al. | |
| 4,968,299 A | 11/1990 | Ahlstrand et al. | 5,396,883 A | 3/1995 | Knupp et al. | |
| 4,971,665 A | 11/1990 | Sexton | 5,414,075 A | 5/1995 | Swan et al. | |
| 4,973,493 A | 11/1990 | Guire | 5,415,161 A * | 5/1995 | Ryder | 128/200.23 |
| 4,976,259 A | 12/1990 | Higson et al. | 5,419,315 A | 5/1995 | Rubsamen | |
| 4,979,959 A | 12/1990 | Guire | 5,426,458 A | 6/1995 | Wenzel et al. | |
| 4,994,043 A | 2/1991 | Ysebaert | 5,431,155 A | 7/1995 | Marelli | |
| 5,002,048 A | 3/1991 | Makiej et al. | 5,435,282 A | 7/1995 | Haber et al. | |
| 5,002,582 A | 3/1991 | Guire et al. | 5,435,297 A | 7/1995 | Klein | |
| 5,007,419 A | 4/1991 | Weinstein et al. | 5,437,267 A | 8/1995 | Weinstein et al. | |
| 5,016,024 A | 5/1991 | Lam et al. | 5,445,141 A | 8/1995 | Kee et al. | |
| 5,021,701 A | 6/1991 | Takahashi et al. | D362,390 S | 9/1995 | Weiler | |
| 5,022,587 A | 6/1991 | Hochstein | 5,449,502 A | 9/1995 | Igusa et al. | |
| 5,024,733 A | 6/1991 | Abys et al. | 5,452,711 A | 9/1995 | Gault | |
| 5,046,627 A | 9/1991 | Hansen | 5,458,135 A | 10/1995 | Patton et al. | |
| 5,062,419 A | 11/1991 | Rider | 5,458,289 A | 10/1995 | Cater | |
| 5,063,396 A | 11/1991 | Shiokawa et al. | 5,474,059 A | 12/1995 | Cooper | |
| 5,063,922 A | 11/1991 | Hakkinen | 5,477,992 A | 12/1995 | Jinks et al. | |
| 5,073,484 A | 12/1991 | Swanson et al. | 5,479,920 A | 1/1996 | Piper et al. | |
| 5,076,266 A | 12/1991 | Babaev | 5,482,030 A | 1/1996 | Klein | |
| 5,080,093 A | 1/1992 | Raabe et al. | 5,485,850 A | 1/1996 | Dietz | |
| 5,080,649 A | 1/1992 | Vetter | 5,487,378 A | 1/1996 | Robertson et al. | |
| 5,086,765 A | 2/1992 | Levine | 5,489,266 A | 2/1996 | Grimard | |
| 5,086,785 A | 2/1992 | Gentile et al. | 5,497,944 A | 3/1996 | Weston et al. | |
| 5,099,833 A | 3/1992 | Michaels et al. | D369,212 S | 4/1996 | Snell | |
| 5,115,803 A | 5/1992 | Sioutas | 5,508,269 A | 4/1996 | Smith et al. | |
| 5,115,971 A | 5/1992 | Greenspan et al. | 5,511,726 A | 4/1996 | Greenspan et al. | |
| D327,008 S | 6/1992 | Friedman | 5,512,329 A | 4/1996 | Guire et al. | |
| 5,122,116 A | 6/1992 | Kriesel et al. | 5,512,474 A | 4/1996 | Clapper et al. | |
| 5,129,579 A | 7/1992 | Conte | 5,515,841 A | 5/1996 | Robertson et al. | |
| 5,134,993 A | 8/1992 | Van Der Linden et al. | 5,515,842 A | 5/1996 | Ramseyer et al. | |
| 5,139,016 A | 8/1992 | Waser | 5,516,043 A | 5/1996 | Manna et al. | |
| 5,140,740 A | 8/1992 | Weigelt | 5,518,179 A | 5/1996 | Humberstone et al. | |
| 5,147,073 A | 9/1992 | Cater | 5,529,055 A | 6/1996 | Gueret | |
| 5,152,456 A | 10/1992 | Ross et al. | 5,533,497 A | 7/1996 | Ryder | |
| 5,157,372 A | 10/1992 | Langford | 5,542,410 A | 8/1996 | Goodman et al. | |
| 5,164,740 A | 11/1992 | Ivri | 5,549,102 A | 8/1996 | Lintl et al. | |
| 5,169,029 A | 12/1992 | Behar et al. | 5,560,353 A * | 10/1996 | Willemot et al. | 128/204.21 |
| 5,170,782 A | 12/1992 | Kocinski | 5,560,837 A | 10/1996 | Trueba | |
| 5,180,482 A | 1/1993 | Abys et al. | 5,563,056 A | 10/1996 | Swan et al. | |
| 5,186,164 A | 2/1993 | Raghuprasad | D375,352 S | 11/1996 | Bologna | |
| 5,186,166 A | 2/1993 | Riggs et al. | 5,570,682 A | 11/1996 | Johnson | |
| 5,198,157 A | 3/1993 | Bechet | 5,579,757 A | 12/1996 | McMahon et al. | |
| 5,201,322 A | 4/1993 | Henry et al. | 5,582,330 A | 12/1996 | Iba | |
| 5,213,860 A | 5/1993 | Laing | 5,584,285 A | 12/1996 | Salter et al. | |
| 5,217,148 A | 6/1993 | Cater | 5,586,550 A | 12/1996 | Ivri et al. | |
| 5,217,492 A | 6/1993 | Guire et al. | 5,588,166 A | 12/1996 | Burnett | |
| 5,227,168 A | 7/1993 | Chvapil | 5,598,836 A | 2/1997 | Larson et al. | |
| 5,230,496 A | 7/1993 | Shillington et al. | 5,601,077 A | 2/1997 | Imbert | |
| 5,241,954 A | 9/1993 | Glenn | 5,609,798 A | 3/1997 | Liu et al. | |
| 5,245,995 A | 9/1993 | Sullivan et al. | 5,617,844 A | 4/1997 | King | |
| 5,248,087 A | 9/1993 | Dressler | 5,632,878 A | 5/1997 | Kitano | |
| 5,258,041 A | 11/1993 | Guire et al. | 5,635,096 A | 6/1997 | Singer et al. | |
| 5,261,601 A | 11/1993 | Ross et al. | 5,637,460 A | 6/1997 | Swan et al. | |
| 5,263,992 A | 11/1993 | Guire | 5,647,349 A | 7/1997 | Ohki et al. | |
| 5,279,568 A | 1/1994 | Cater | 5,653,227 A | 8/1997 | Barnes et al. | |
| 5,287,849 A | 2/1994 | Piper et al. | 5,654,007 A | 8/1997 | Johnson et al. | |
| 5,297,734 A | 3/1994 | Toda | 5,654,162 A | 8/1997 | Guire et al. | |
| 5,299,739 A | 4/1994 | Takahashi et al. | 5,654,460 A | 8/1997 | Rong | |
| 5,303,854 A | 4/1994 | Cater | 5,657,926 A | 8/1997 | Toda | |
| 5,304,125 A | 4/1994 | Leith | 5,660,166 A | 8/1997 | Lloyd | |
| 5,309,135 A | 5/1994 | Langford | 5,664,557 A | 9/1997 | Makiej, Jr. | |
| 5,312,281 A | 5/1994 | Takahashi et al. | 5,664,706 A | 9/1997 | Cater | |
| 5,313,955 A | 5/1994 | Rodder | 5,665,068 A | 9/1997 | Takamura | |
| 5,319,971 A | 6/1994 | Osswald et al. | 5,666,946 A | 9/1997 | Langenback | |
| 5,320,603 A | 6/1994 | Vetter et al. | 5,670,999 A | 9/1997 | Takeuchi et al. | |
| 5,322,057 A | 6/1994 | Raabe et al. | 5,685,491 A | 11/1997 | Marks et al. | |
| 5,342,011 A | 8/1994 | Short | 5,692,644 A | 12/1997 | Gueret | |
| 5,342,504 A | 8/1994 | Hirano et al. | 5,694,920 A | 12/1997 | Abrams et al. | |
| 5,347,998 A | 9/1994 | Hodson et al. | 5,707,818 A | 1/1998 | Chudzik et al. | |
| 5,348,189 A | 9/1994 | Cater | 5,709,202 A | 1/1998 | Lloyd et al. | |
| 5,350,116 A | 9/1994 | Cater | 5,714,360 A | 2/1998 | Swan et al. | |
| 5,355,872 A | 10/1994 | Riggs et al. | 5,714,551 A | 2/1998 | Bezwada et al. | |
| 5,357,946 A | 10/1994 | Kee et al. | 5,718,222 A | 2/1998 | Lloyd et al. | |
| 5,372,126 A | 12/1994 | Blau | D392,184 S | 3/1998 | Weiler | |

| | | | | | | |
|---|---|---|---|---|---|---|
| 5,724,957 | A | 3/1998 | Rubsamen et al. | 6,223,746 | B1 | 5/2001 | Jewett et al. |
| 5,744,515 | A | 4/1998 | Clapper | 6,235,177 | B1 | 5/2001 | Borland et al. |
| 5,752,502 | A | 5/1998 | King | 6,254,219 | B1 | 7/2001 | Agarwal et al. |
| 5,755,218 | A | 5/1998 | Johansson et al. | 6,260,549 | B1 | 7/2001 | Sosiak |
| 5,758,637 | A * | 6/1998 | Ivri et al. ............... 128/200.16 | 6,269,810 | B1 * | 8/2001 | Brooker et al. .......... 128/203.12 |
| 5,775,506 | A | 7/1998 | Grabenkort | 6,270,473 | B1 | 8/2001 | Schwebel |
| 5,788,665 | A | 8/1998 | Sekins | 6,273,342 | B1 | 8/2001 | Terada et al. |
| 5,788,819 | A | 8/1998 | Onishi et al. | 6,315,397 | B2 | 11/2001 | Truninger et al. |
| 5,790,151 | A | 8/1998 | Mills | 6,318,361 | B1 | 11/2001 | Sosiak |
| 5,797,389 | A | 8/1998 | Ryder | 6,318,640 | B1 | 11/2001 | Coffee |
| 5,810,004 | A | 9/1998 | Ohki et al. | 6,328,030 | B1 | 12/2001 | Kidwell et al. |
| 5,819,730 | A | 10/1998 | Stone et al. | 6,328,033 | B1 | 12/2001 | Avrahami |
| 5,823,179 | A | 10/1998 | Grychowski et al. | 6,336,453 | B1 | 1/2002 | Scarrott et al. |
| 5,823,428 | A | 10/1998 | Humberstone et al. | 6,341,732 | B1 | 1/2002 | Martin et al. |
| 5,829,723 | A | 11/1998 | Brunner et al. | 6,358,058 | B1 | 3/2002 | Strupat et al. |
| 5,836,515 | A | 11/1998 | Fonzes | 6,367,470 | B1 | 4/2002 | Denyer |
| 5,839,617 | A | 11/1998 | Cater et al. | 6,387,886 | B1 | 5/2002 | Montgomery et al. |
| 5,842,468 | A | 12/1998 | Denyer et al. | 6,390,091 | B1 * | 5/2002 | Banner et al. ............ 128/204.21 |
| 5,848,587 | A | 12/1998 | King | 6,394,363 | B1 | 5/2002 | Arnott et al. |
| 5,862,802 | A | 1/1999 | Bird | 6,402,046 | B1 | 6/2002 | Loser |
| 5,865,171 | A | 2/1999 | Cinquin | 6,405,934 | B1 | 6/2002 | Hess et al. |
| 5,878,900 | A | 3/1999 | Hansen | 6,412,481 | B1 | 7/2002 | Bienvenu et al. |
| 5,893,515 | A | 4/1999 | Hahn et al. | 6,427,682 | B1 | 8/2002 | Klimowicz et al. |
| 5,894,841 | A | 4/1999 | Voges | 6,443,146 | B1 | 9/2002 | Voges |
| 5,897,008 | A | 4/1999 | Hansen | 6,443,366 | B1 | 9/2002 | Hirota et al. |
| 5,910,698 | A | 6/1999 | Yagi | 6,467,476 | B1 | 10/2002 | Ivri et al. |
| 5,915,377 | A | 6/1999 | Coffee | 6,516,798 | B1 | 2/2003 | Davies |
| 5,918,637 | A | 7/1999 | Fleischman | 6,530,370 | B1 | 3/2003 | Heinonen |
| 5,921,232 | A | 7/1999 | Yokoi et al. | 6,539,937 | B1 | 4/2003 | Haveri |
| 5,925,019 | A | 7/1999 | Ljungquist | 6,540,153 | B1 | 4/2003 | Ivri |
| 5,938,117 | A | 8/1999 | Ivri | 6,540,154 | B1 | 4/2003 | Ivri et al. |
| 5,950,619 | A | 9/1999 | Van Der Linden et al. | 6,543,443 | B1 | 4/2003 | Klimowicz et al. |
| 5,954,268 | A | 9/1999 | Joshi et al. | 6,546,927 | B2 | 4/2003 | Litherland et al. |
| 5,960,792 | A | 10/1999 | Lloyd et al. | 6,550,472 | B2 | 4/2003 | Litherland et al. |
| 5,964,417 | A | 10/1999 | Amann et al. | 6,554,201 | B2 | 4/2003 | Klimowicz et al. |
| 5,970,974 | A | 10/1999 | Van Der Linden et al. | 6,576,224 | B1 | 6/2003 | Osbakken et al. |
| 5,976,344 | A | 11/1999 | Abys et al. | 6,578,571 | B1 | 6/2003 | Watt |
| 5,993,805 | A | 11/1999 | Sutton et al. | 6,581,595 | B1 | 6/2003 | Murdock et al. |
| 6,000,396 | A | 12/1999 | Melker et al. | 6,596,261 | B1 | 7/2003 | Adjei et al. |
| 6,006,745 | A | 12/1999 | Marecki | 6,598,602 | B1 | 7/2003 | Sjoholm |
| 6,007,518 | A | 12/1999 | Kriesel et al. | 6,601,581 | B1 | 8/2003 | Babaev |
| 6,012,450 | A | 1/2000 | Rubsamen | 6,606,989 | B1 * | 8/2003 | Brand et al. ............. 128/200.16 |
| 6,014,970 | A | 1/2000 | Ivri et al. | 6,612,303 | B1 | 9/2003 | Grychowski et al. |
| 6,026,809 | A | 2/2000 | Abrams et al. | 6,615,824 | B2 | 9/2003 | Power |
| 6,029,666 | A | 2/2000 | Aloy et al. | 6,629,646 | B1 | 10/2003 | Ivri |
| 6,032,665 | A | 3/2000 | Psaros | 6,631,721 | B1 | 10/2003 | Salter et al. |
| 6,037,587 | A | 3/2000 | Dowell et al. | 6,640,804 | B2 | 11/2003 | Ivri |
| 6,039,696 | A | 3/2000 | Bell | 6,644,304 | B2 | 11/2003 | Grychowski et al. |
| 6,044,841 | A | 4/2000 | Verdun et al. | 6,651,650 | B1 | 11/2003 | Yamamoto et al. |
| 6,045,215 | A | 4/2000 | Cooulman | 6,694,978 | B1 | 2/2004 | Bennarsten |
| 6,045,874 | A | 4/2000 | Himes | 6,705,315 | B2 | 3/2004 | Sullivan et al. |
| 6,047,818 | A | 4/2000 | Warby et al. | 6,732,944 | B2 | 5/2004 | Litherland et al. |
| 6,055,869 | A | 5/2000 | Stemme et al. | 6,745,768 | B2 | 6/2004 | Colla et al. |
| 6,060,128 | A | 5/2000 | Kim et al. | 6,745,770 | B2 | 6/2004 | McAuliffe et al. |
| 6,062,212 | A | 5/2000 | Davison et al. | 6,755,189 | B2 | 6/2004 | Ivri et al. |
| 6,068,148 | A | 5/2000 | Weiler | 6,761,161 | B2 | 7/2004 | Scarrott et al. |
| 6,085,740 | A | 7/2000 | Ivri et al. | 6,769,626 | B1 | 8/2004 | Haveri |
| 6,096,011 | A | 8/2000 | Trombley, III et al. | 6,776,155 | B2 | 8/2004 | Farrell et al. |
| 6,105,877 | A | 8/2000 | Coffee | 6,782,886 | B2 | 8/2004 | Narayan et al. |
| 6,106,504 | A | 8/2000 | Urrutia | 6,810,876 | B2 | 11/2004 | Berthon-Jones |
| 6,116,234 | A | 9/2000 | Genova et al. | 6,814,071 | B2 | 11/2004 | Klimowicz et al. |
| 6,123,413 | A | 9/2000 | Agarwal et al. | 6,817,361 | B2 | 11/2004 | Berthon-Jones et al. |
| 6,139,674 | A | 10/2000 | Markham et al. | 6,840,240 | B1 | 1/2005 | Berthon-Jones et al. |
| 6,142,146 | A | 11/2000 | Abrams et al. | 6,845,770 | B2 | 1/2005 | Klomowicz et al. |
| 6,145,963 | A | 11/2000 | Pidwerbecki et al. | 6,851,626 | B2 | 2/2005 | Patel et al. |
| 6,146,915 | A | 11/2000 | Pidwerbecki et al. | 6,860,268 | B2 | 3/2005 | Bohn et al. |
| 6,152,130 | A | 11/2000 | Abrams et al. | 6,915,962 | B2 | 7/2005 | Power et al. |
| 6,155,676 | A | 12/2000 | Etheridge et al. | 6,921,020 | B2 | 7/2005 | Ivri |
| 6,158,431 | A | 12/2000 | Poole | 6,926,208 | B2 | 8/2005 | Ivri |
| 6,161,536 | A | 12/2000 | Redmon et al. | 6,948,491 | B2 | 9/2005 | Loeffler et al. |
| 6,163,588 | A | 12/2000 | Matsumoto et al. | 6,968,840 | B2 | 11/2005 | Smith et al. |
| 6,182,662 | B1 | 2/2001 | McGhee | 6,978,941 | B2 | 12/2005 | Litherland et al. |
| 6,186,141 | B1 | 2/2001 | Pike et al. | 7,100,600 | B2 | 9/2006 | Loeffler et al. |
| 6,196,218 | B1 | 3/2001 | Voges | 7,156,917 | B2 | 1/2007 | Moriyama et al. |
| 6,196,219 | B1 | 3/2001 | Hess et al. | 7,267,121 | B2 | 9/2007 | Ivri |
| 6,205,999 | B1 | 3/2001 | Ivri et al. | 2001/0013554 | A1 | 8/2001 | Borland et al. |
| 6,216,025 | B1 | 4/2001 | Kruger | 2001/0015737 | A1 | 8/2001 | Truninger et al. |
| 6,216,690 | B1 * | 4/2001 | Keitel et al. ............. 128/203.12 | 2002/0011247 | A1 | 1/2002 | Ivri et al. |
| 6,216,916 | B1 | 4/2001 | Maddox et al. | 2002/0023639 | A1 | 2/2002 | Ivri et al. |

| | | | |
|---|---|---|---|
| 2002/0023650 A1 | 2/2002 | Gunaratnam et al. | |
| 2002/0033178 A1 | 3/2002 | Farrell et al. | |
| 2002/0036601 A1 | 3/2002 | Puckeridge et al. | |
| 2002/0078958 A1 | 6/2002 | Stenzler | |
| 2002/0088461 A1 | 7/2002 | Alksnis | |
| 2002/0104530 A1 | 8/2002 | Ivri et al. | |
| 2002/0121274 A1 | 9/2002 | Borland et al. | |
| 2002/0134372 A1 | 9/2002 | Loeffler et al. | |
| 2002/0134374 A1 | 9/2002 | Loeffler et al. | |
| 2002/0134375 A1 | 9/2002 | Loeffler et al. | |
| 2002/0134377 A1 | 9/2002 | Loeffler et al. | |
| 2002/0162551 A1 | 11/2002 | Litherland | |
| 2002/0162554 A1 | 11/2002 | Loescher | |
| 2002/0195107 A1 | 12/2002 | Smaldone | |
| 2003/0140921 A1 | 7/2003 | Smith et al. | |
| 2003/0145859 A1 | 8/2003 | Bohn et al. | |
| 2003/0150445 A1 | 8/2003 | Power et al. | |
| 2003/0150446 A1 | 8/2003 | Patel et al. | |
| 2003/0205229 A1 | 11/2003 | Crockford | |
| 2003/0226906 A1 | 12/2003 | Ivri | |
| 2004/0000598 A1 | 1/2004 | Ivri | |
| 2004/0004133 A1 | 1/2004 | Ivri et al. | |
| 2004/0011358 A1 | 1/2004 | Smaldone et al. | |
| 2004/0035413 A1 | 2/2004 | Smaldone et al. | |
| 2004/0035490 A1 | 2/2004 | Power | |
| 2004/0050947 A1 | 3/2004 | Power et al. | |
| 2004/0123974 A1 | 7/2004 | Marler et al. | |
| 2004/0139963 A1 | 7/2004 | Ivri et al. | |
| 2004/0139968 A1 | 7/2004 | Loeffler et al. | |
| 2004/0188534 A1 | 9/2004 | Litherland et al. | |
| 2004/0194783 A1 | 10/2004 | McAuliffe et al. | |
| 2004/0226561 A1 | 11/2004 | Colla et al. | |
| 2004/0226566 A1 | 11/2004 | Gunaratnam et al. | |
| 2004/0256488 A1 | 12/2004 | Loeffler et al. | |
| 2005/0011514 A1 | 1/2005 | Power et al. | |
| 2005/0039746 A1 | 2/2005 | Grychowski et al. | |
| 2005/0139211 A1 | 6/2005 | Alston et al. | |
| 2005/0150496 A1 | 7/2005 | Smaldone | |
| 2005/0172954 A1 | 8/2005 | Smith et al. | |
| 2005/0178847 A1 | 8/2005 | Power et al. | |
| 2005/0211245 A1 | 9/2005 | Smaldone et al. | |
| 2005/0211253 A1 | 9/2005 | Smaldone et al. | |
| 2005/0217666 A1 | 10/2005 | Fink et al. | |
| 2005/0220763 A1 | 10/2005 | Condos et al. | |
| 2005/0229927 A1 | 10/2005 | Fink et al. | |
| 2005/0229928 A1 | 10/2005 | Ivri et al. | |
| 2005/0235987 A1 | 10/2005 | Smaldone et al. | |
| 2005/0279851 A1 | 12/2005 | Ivri | |

FOREIGN PATENT DOCUMENTS

| | | |
|---|---|---|
| CH | 477 885 | 9/1969 |
| CH | 555 681 | 11/1974 |
| DE | 11 03 522 | 3/1961 |
| EP | 0 049 636 | 4/1982 |
| EP | 0 103 161 | 3/1984 |
| EP | 0 134 847 | 3/1985 |
| EP | 0 178 925 | 4/1986 |
| EP | 0 387 222 | 9/1990 |
| EP | 0 432 992 | 6/1991 |
| EP | 0 476 991 | 3/1992 |
| EP | 0 480 615 | 4/1992 |
| EP | 0 510 648 | 10/1992 |
| EP | 0 516 565 | 12/1992 |
| EP | 0 542 723 | 5/1993 |
| EP | 0 933 138 | 4/1999 |
| EP | 0 923 957 | 6/1999 |
| EP | 1 142 600 | 10/2001 |
| FR | 2622113 A | 4/1989 |
| FR | 2624017 A | 6/1989 |
| FR | 2 692 569 | 12/1993 |
| GB | 973 458 | 10/1964 |
| GB | 1 454 597 | 11/1976 |
| GB | 2 073 616 | 10/1981 |
| GB | 2 101 500 | 1/1983 |
| GB | 2 177 623 | 1/1987 |
| GB | 2 240 494 | 7/1991 |
| GB | 2 272 389 | 5/1994 |
| GB | 2 279 571 | 1/1995 |
| JP | 57-023852 | 2/1982 |
| JP | 57-105608 | 7/1982 |
| JP | 58-061857 | 4/1983 |
| JP | 58-139757 | 8/1983 |
| JP | 59-142163 | 8/1984 |
| JP | 60-004714 | 1/1985 |
| JP | 61-008357 | 1/1986 |
| JP | 61-215059 | 9/1986 |
| JP | 02-135169 | 5/1990 |
| JP | 02-189161 | 7/1990 |
| JP | 60-07721 | 1/1994 |
| WO | WO 82/03548 | 10/1982 |
| WO | WO 92/07600 | 5/1992 |
| WO | WO 92/11050 | 9/1992 |
| WO | WO 92/17231 | 10/1992 |
| WO | WO 93/01404 | 1/1993 |
| WO | WO 93/10910 | 6/1993 |
| WO | WO 94/09912 | 5/1994 |
| WO | WO 96/09229 | 3/1996 |
| WO | WO9707896 | 3/1997 |
| WO | WO 99/17888 | 4/1999 |
| WO | WO9963746 | 12/1999 |
| WO | WO9963946 | 12/1999 |
| WO | WO 00/37132 | 6/2000 |
| WO | WO0118280 | 3/2001 |
| WO | WO 03/059424 | 7/2003 |

OTHER PUBLICATIONS

Lucent Technologies, "PallaTech—Procedure for the Analysis of Additive IVS in PallaTech Plating Solutions by HPLC," Technical Bulletin, TB:029-A, pp. cover and 1-5, Oct. 1, 1996.

Palmer et al., Aerosolized antibiotics in mechanically ventilated patients: Deliver and response, 1998, Crit Care Med., vol. 26, No. 1, pp. 31-39.

TSI Incorporated, "Vibrating Orifice Aerosol Generator," 4 pages 1989.

Abys, et al., "Annealing Behavior of Palladium-Nickel Alloy Electrodeposits," Plating and Surface Finishing, Aug. 1996; pp. 1-7.

Allen, "Particle Size Measurement," 3rd Edition, Chapman and Hall, 1981; pp. 167-169.

Ashgriz, et al., "Development of a Controlled Spray Generator," Rev. Sci. Instrum. 1987; pp. 1291-1296, vol. 58, No. 7.

Berggren, "Pilot Study of Nebulized Surfactant Therapy for Neonatal Respiratory Distress Syndrome," Acta Paediatr 89: 460-464, Taylor & Francis, ISSN 0803-5253, 2000; Sweden.

Berglund, et al., "Generation of Monodisperse Aerosol Standards," Environ. Sci. Tech., Feb. 1973; pp. 147-153, vol. 7, No. 2.

Cipolla, et al., "Assessment of Aerosol Delivery Systems for Recombinant Human Deoxyribonuclease," S.T.P. Pharma Sciences, 1994; pp. 50-62, vol. 4, No. 1.

Cipolla, et al., "Characterization of Aerosols of Human Recombinant Deoxyribonuclease (rhDNase) Generated by Neulizers," Pharmaceutical Research II, 1994; pp. 491-498, vol. 4.

Dogan, "Thesis: Flexional 'Moonie and Cymbal' Actuators", Penn State Univ., 1994.

Duarte, et al., "Inhalation Therapy During Mechanical Ventilation," Resp. Care, Clinics of North America, Aerosol Therapy, Jun. 2001; pp. 233-259, vol. 7, No. 2.

Fink, et al., "Aerosol Drug Therapy," Clinical Practice in Respiratory Care, 1999; Chapter 12, pp. 308-342.

Fink, et al., "Aerosol Therapy in Mechanically Ventilated Patients: Recent Advances and New Techniques," Seminars in Respiratory and Critical Care Medicine, 2000; pp. 183-201, vol. 21, No. 3.

Fink, et al., "Diagram from and abstract of article entitled" Optimizing efficiency of nebulizers during mechanical ventilation: The effect of placement and type of ventilator circuit, Chest, Oct. 1999; 116:312S.

Gaiser Tool Company Catalog, pp. 26, 29-30, 1990.

Gonda, "Therapeutic," Pharmaceuticals, The Science of Dosage Form Design, Editor: M.E. Aulton, 1988; pp. 341-358.

Hancock, et al., "Molecular Mobility of Amorphous Pharmaceutical Solids Below Their Glass Transition Temperatures," Pharmaceutical Research 12, 1995; pp. 799-806.

Heyder, et al., "Deposition of particles in the human respiratory tract in the size range 0.005-15 microns," J. Aerosol Sci., 1986; pp. 811-825, vol. 17.

Hickey, "Pharmaceutical Inhalation Aerosol Technology," Drugs and the Pharmaceutical Science, 1992; pp. 172-173, vol. 54.

Hikayama, et al., "Ultrasonic Atomizer with Pump Function," Tech. Rpt, IEICE Japan US88-74:25, 1988. (No English Translation Available).

Jorch, "Letter to the Editor, Surfactant Aerosol Treatment of Respiratory Distress Syndrome in Spontaneously Breathing Premature Infants," Pediatric Pulmonology, 1997; pp. 222-224, vol. 24, Wiley-Liss.

Maehara, et al., "Atomizing rate control of a multi-pinhole-plate ultrasonic atomizer," J. Acoustical Soc. Japan, 1988; pp. 116-121, vol. 44, No. 2.

Maehara, et al., "Influence of the vibrating system of a multipinhole-plate ultrasonic nebulizer on its performance," Review of Scientific Instruments, Nov. 1986; pp. 2870-2876, vol. 57, No. 1.

Maehara, et al., "Influences of liquid's physical properties on the characteristics of a multi-pinhole-plate ultrasonic atomizer," J. Acoustical Soc. Japan, 1988; pp. 425-431, vol. 44, No. 6.

Maehara, et al., "Optimum Design Procedure for Multi-Pinhole-Plate Ultrasonic Atomizer," Japanese Journal of Applied Physics, 1987; pp. 215-217, vol. 26, Supp. 26-1.

Manning, et al., "Stability of Protein Pharmaceuticals," Pharmaceutical Research 6, 1989; pp. 903-918.

Mercier, et al., "Aerosol Delivery of Amikacin by Three Nebulizers of Varying Efficiency in Patients on Mechanical Ventilators," Internet Artical (online), May 2004; URL: http://www.aerogen.com/publications/2004.htm.

Nogi, et al., "Mixture Formation of Fuel Injection System in Gasoline Engine," Nippon Kikai Gakkai Zenkoku Taikai Koenkai Koen Ronbunshu, 1991; pp. 660-662, vol. 69.

Palla Tech Pd an Pd Alloy Processes-Procedure for the Analysis of Additive IVS in Palla Tech Plating Solutions by HPLC, Technical Bulletin, Electroplating Chemicals & Services, 029-A, Lucent Technologies, pp. 1-5, 1996.

Siemens, Servo Ultra Nebulizer 345 Operating Manual, pp. 1-23.

Smaldone, et al., "Aerosolized Antibiotics: Current and Future," Respiratory Care, 2000; pp. 667-675, vol. 45, No. 6.

Smedsaas-Lofvenbert, "Nebulizzation of Drugs in a Nasal CPAP System," Scandinavian University Press, 1999; Acta Paediatr 88: 89-92, Sweden.

Ueha, et al., "Mechanism of Ultrasonic Atomization Using a Multi-Pinhole Plate," J. Acoust. Soc. Jpn., 1985; pp. 21-26, (E)6,1.

Wehl, "Ink-Jet-Printing: The Present State of the Art," for Siemens AG, 1989.

* cited by examiner

```
┌─────────────────────────────────────┐
│   TAKING ONE OR MORE BREATHS        │─── 1320
└─────────────────────────────────────┘
                  │
┌─────────────────────────────────────┐
│    MEASURING CHARACTERISTICS        │─── 1322
│         OF THE BREATH               │
└─────────────────────────────────────┘
                  │
┌─────────────────────────────────────┐
│ TAKING ANOTHER BREATH AND OPERATING │
│   AN AEROSOL GENERATOR BASED ON THE │─── 1324
│ MEASURED CHARACTERISTICS OF THE BREATH│
└─────────────────────────────────────┘
```

FIG.13

```
                                    1400
          1402                   ┌────────┐
       ┌────────┐               / SELECT  \         ┌────────────┐
       │REGIME I│              /  REGIME   \        │  REGIME II │
       │CONTINUOUS│◄──────────<   FOR       >─────► │- FOR ENTIRE│
       │ AEROSOL │              \ AEROSOL  /        │ INHALATION │
       │GENERATION│              \GENERATION/       │   PHASE    │
       └────┬────┘                 \──┬───/         └──────┬─────┘
            │                     1404                    │
            ▼                                             ▼
       ┌─────────────┐                          ┌──────────────────┐
       │  REGIME III │                          │  SET AEROSOL     │
       │ - DURING A  │── 1416          1406 ──│ GENERATION TO BEGIN│
       │PREDETERMINED│                          │ UPON COMMENCEMENT│
       │PERCENTAGE OF│                          │ OF INHALATION PHASE│
       │INHALATION PHASE│                       └──────┬───────────┘
       └──────┬──────┘                                 │
              ▼                                        ▼
       ┌─────────────┐                          ┌──────────────────┐
       │ SET A FIRST │                          │  SET AEROSOL     │
       │PREDETERMINED│── 1418          1408 ──│ GENERATION TO STOP │
       │POINT DURING│                           │ UPON ENDING OF   │
       │INHALATION - TO│                        │ INHALATION PHASE │
       │START AEROSOLIZATION│                   └──────┬───────────┘
       └──────┬──────┘                                 │
              ▼                                        ▼
       ┌─────────────┐                          ┌──────────────────┐
       │SET A SECOND │                          │ BEGIN AEROSOL    │
       │PREDETERMINED│── 1420          1410 ──│ GENERATION AT THE  │
       │POINT DURING │                          │ START OF THE     │
       │INHALATION - TO│                        │ INHALATION PHASE │
       │START AEROSOLIZATION│                   └──────┬───────────┘
       └──────┬──────┘                                 │
              ▼                                        ▼
       ┌─────────────┐                              1412
       │BEGIN AEROSOL│                          ╱────────╲
       │GENERATION AT│── 1422                  ╱  END OF  ╲
       │   THE FIRST │                        <  INHALATION >
       │PREDETERMINED POINT│                   ╲   PHASE   ╱
       └──────┬──────┘                          ╲────┬────╱
              ▼                                      │
          1424                                      1414
       ╱────────╲                              ┌──────────────┐
      ╱ SECOND   ╲                             │STOP AEROSOL  │
     < PREDETERMINED>──────────────────────────►│GENERATION UNTIL│
      ╲  POINT   ╱                             │ NEXT CYCLE   │
       ╲REACHED ╱                              └──────────────┘
        ╲──┬──╱
           └──────────────────────────────────┘

FIG.14
```

```
                    ┌─────────────────┐
                    │ PROVIDE LIBRARY OF│
                    │   REGIMES BASED  │
                    │  ON THE DRUG TO  │
                    │  BE ADMINISTERED │
                    └────────┬─────────┘
                         1700─┘
                              │
                              ▼
                    ┌─────────────────┐        ┌──────────────────┐
                    │ PROVIDE IDENTITY│        │  CONTROLLER LOOKS│
                    │ OF A SELECTED DRUG├─────►│  UP A REGIME FROM│
                    │ TO BE AEROSOLIZED│        │ THE LIBRARY BASED│
                    └────────┬─────────┘        │   ON THE IDENTITY│
                         1702─┘                 │    OF THE DRUG   │
                                                └────────┬─────────┘
                                                     1704─┘
                                                          │
                                                          ▼
                                                ┌──────────────────┐
                                                │ CONTROLLER RECEIVES│
                                                │  SIGNAL THAT THE │
                                                │ VENTILATOR HAS BEGUN│
                                                │    TO SUPPLY AN  │
                                                │  INHALATION PHASE│
                                                └────────┬─────────┘
                                                     1706─┘
```

FIG.17

(Flow chart, Fig. 17)

- 1700: PROVIDE LIBRARY OF REGIMES BASED ON THE DRUG TO BE ADMINISTERED
- 1702: PROVIDE IDENTITY OF A SELECTED DRUG TO BE AEROSOLIZED
- 1704: CONTROLLER LOOKS UP A REGIME FROM THE LIBRARY BASED ON THE IDENTITY OF THE DRUG
- 1706: CONTROLLER RECEIVES SIGNAL THAT THE VENTILATOR HAS BEGUN TO SUPPLY AN INHALATION PHASE
- 1708: CONTROLLER CHOOSES AN OPERATION SEQUENCE BASED IN PART ON THE IDENTITY OF THE DRUG AND IN PART ON THE SIGNAL FROM THE VENTILATOR
- 1710: CONTROLLER CARRIES OUT THE OPERATION SEQUENCE TO PROVIDE AEROSOLIZED DRUG INTO THE VENTILATOR CIRCUIT, BASED ON A STORED REGIME FOR THAT DRUG, AT A PREDETERMINED INTERVAL IN A VENTILATOR CYCLE

METHODS AND SYSTEMS FOR OPERATING AN AEROSOL GENERATOR

CROSS-REFERENCES TO RELATED APPLICATIONS

This application is a continuation of prior U.S. patent application Ser. No. 11/090,328, filed Mar. 24, 2005, which is a continuation-in-part of U.S. patent application Ser. No. 10/345,875, filed Jan. 15, 2003, now U.S. Pat. No. 6,968,840, Ser. No. 09/849,194, filed May 4, 2001, now U.S. Pat. No. 6,615,824, Ser. No. 09/812,755, filed Mar. 20, 2001, now U.S. Pat. No. 7,100,600 and Ser. No. 10/284,068, filed Oct. 30, 2002, now U.S. Pat. No. 7,600,511. The entire content of all of the aforementioned applications are herein incorporated by reference for all purposes.

U.S. patent application Ser. No. 11/090,328 is related to U.S. patent application Ser. No. 09/876,542, filed Jun. 7, 2001, now abandoned, Ser. No. 09/876,402, filed Jun. 7, 2001, now abandoned, and Ser. No. 09/812,987, filed Mar. 20, 2001, now U.S. Pat. No. 6,948,491, which are incorporated herein by reference, in their entirety, for all purposes.

U.S. patent application Ser. No. 09/849,194, now U.S. Pat. No. 6,615,824, claims the benefit of Patent Cooperation Treaty Application No. PCT/IE/00051, filed May 5, 2000, which is incorporated herein by reference, in its entirety, for all purposes.

U.S. patent application Ser. No. 10/284,068, now U.S. Pat. No. 7,600,511, claims the benefit of U.S. Provisional Application Nos. 60/344,484, filed Nov. 1, 2001, and 60/381,830, filed May 20, 2002, which are incorporated herein by reference, in their entirety, for all purposes.

FIELD OF THE INVENTION

The present invention generally relates to systems and methods for the delivery of aerosolized medicaments. More specifically, embodiments of the invention relate to the coupling of aerosol generators with ventilator circuits, permitting an aerosolized medicament to be inhaled directly by a patient.

BACKGROUND OF THE INVENTION

Aerosolized medicaments are used to treat patients suffering from a variety of respiratory ailments. Medicaments can be delivered directly to the lungs by having the patient inhale the aerosol through a tube and/or mouthpiece coupled to the aerosol generator. By inhaling the aerosolized medicament, the patient can quickly receive a dose of medicament that is concentrated at the treatment site (e.g., the bronchial passages and lungs of the patient). Generally, this is a more effective and efficient method of treating respiratory ailments than first administering a medicament through the patient's circulatory system (e.g., intravenous injection). However, may problems still exist with the delivery of aerosolized medicaments.

Patients who cannot breathe normally without the aid of a ventilator may only be able to receive aerosolized medicaments through a ventilator circuit. The aerosol generator should therefore be adapted to deliver an aerosol through the ventilator. Unfortunately, medicament delivery efficiencies for combination nebulizer-ventilator systems are quite low, often dropping below 20%. The ventilator circuits typically force the aerosol to travel through a number of valves, conduits, and filters before reaching the patient's mouth or nose, and all the surfaces and obstacles provide a lot of opportunity for aerosol particles to condense back into the liquid phase.

One problem is that conventional aerosolizing technology is not well suited for incorporation into ventilator circuits. Conventional jet and ultrasonic nebulizers normally require 50 to 100 milliseconds to introduce the aerosolized medicament into the circuit. They also tend to produce aerosols with large mean droplet sizes and poor aerodynamic qualities that make the droplets more likely to form condensates on the walls and surfaces of the circuit.

Delivery efficiencies can also suffer when aerosols are being delivered as the patient exhales into the ventilator. Conventional nebulizers deliver constant flows of aerosol into the ventilator circuit, and the aerosol can linger, or even escape from the circuit when the patient is not inhaling. The lingering aerosol is more likely to condense in the system, and eventually be forced out of the circuit without imparting any benefit to the patient.

The failure of substantial amounts of an aerosolized medicament to reach a patient can be problematic for several reasons. First, the dosage of drug actually inhaled by the patient may be significantly inaccurate because the amount of medication the patient actually receives into the patient's respiratory system may vary with fluctuations of the patient's breathing pattern. Further, a significant amount of drug that is aerosolized may end up being wasted, and certain medications are quite costly, thus health-care costs are escalated.

Some of the unused medication may also escape into the surrounding atmosphere. This can end up medicating individuals in proximity to the patient, putting them at risk for adverse health effects. In a hospital environment, these individuals may be health-care providers, who could be exposed to such air pollution over a prolonged period of time, or other patients, who may be in a weakened condition or otherwise sensitive to exposure to unprescribed medications, or an overdose of a medication.

For these reasons, it's desirable to increase the aerosol delivery efficiencies of nebulizer-ventilator systems. Embodiments of the present invention address these and other problems with conventional systems and methods of treating patients with aerosolized medicaments.

BRIEF SUMMARY OF THE INVENTION

The present invention provides devices and methods for improving a level of safety to the patient and for providing an increased efficiency of delivery of an aerosol to the patient.

Embodiments of the invention include a method of treating a patient with a pulmonary disease. The method includes delivering a dose of aerosolized medicament intermittently to a ventilator circuit coupled to the respirator system of the patient.

Embodiments of the invention also include a method of treating a patient with a pulmonary disease by administering to the patient, through a ventilator circuit, a nebulized aerosol comprising from about 100 µg to about 500 mg of a medicament. The efficiency of the method is such that at least 40% of the nebulized aerosol is delivered to the patient.

Embodiments of the invention also include a method of treating a patient with a pulmonary disease by taking the patient off a ventilator, and administering to the patient, a nebulized aerosol comprising from about 100 µg to about 500 mg of a medicament.

Embodiments of the invention still further include methods of treating a pulmonary disease by administering to a patient a medicament comprising an antibiotic dissolved in an aqueous solution comprising sodium chloride that is adjusted to a pH between 5.5 and 6.3. The medicament is administered by nebulization using a vibratable member with apertures, the member configured to produce 70% or more of aerosol particles with mass mean aerodynamic diameters from about 1 µm to about 7 µm.

Embodiments of the invention additionally include a method of treating a patient with a pulmonary disease by administrating an aerosolized medicament to the patient, and administrating, intravenously, a second medicament to the patient that also treats the pulmonary disease.

Embodiments of the invention yet still further include an aerosolized medicament for the treatment of a pulmonary disease. The medicament includes amikacin mixed with an aqueous solution having an adjusted pH from about 5.5 to about 6.3. The pH is adjusted by adding hydrochloric acid and sodium hydroxide to the aqueous solution.

Embodiments also include methods of nebulizing a liquid. The method comprises taking one or more breaths and measuring characteristics of the breath. Another breath is taken and an aerosol generator is operated based on the measured characteristics of the one or more measured breaths.

Still further embodiments of the invention include methods of providing a nebulizer system comprising a housing, an aerosol generator, a controller coupled to the aerosol generator, and a reservoir in communication with the aerosol generator.

In still more embodiments, the present invention provides a nebulizer system comprising a housing that defines a passageway that is adapted to deliver an aerosolized liquid to a user. An aerosol generator is positioned to provide an aerosolized liquid into the passageway. A controller having a memory and a plurality of aerosol generator operation programs that control operation of the aerosol generator is coupled to the aerosol generator.

In yet still more embodiments, the present invention provides a nebulizing element positioned to provide nebulized fluid into a ventilator breathing circuit to provide nebulized fluid to a patient receiving air from a ventilator. It will be appreciated that a nebulizing element may also be referred to herein an aerosolization element, and a ventilator may also be referred to herein as a respirator.

Embodiments of the invention also provide operation sequences by which aerosol is provided a predetermined points in a breath cycle provided by a ventilator. In one aspect, the present invention provides for an operation sequence in which aerosol production begins at a predetermined point within an inhalation phase, which may also be referred to herein as an inspiratory phase, and stops at a second predetermined point within the same inhalation phase. In another aspect, the present invention provides for an operation sequence, which may be referred to as an operation program, in which aerosol production begins at a predetermined point in an inhalation phase and stops at a point after the inhalation phase has ended, i.e. at a certain point in the exhalation phase. It will be appreciated that the exhalation phase may also be referred to as the expiratory phase, and may encompass the entire period of time during which no inhalation phase is taking place; in other words, the exhalation phase may include not only the actual exhalation of the patient, but also any pause that may occur before or after exhalation. In another aspect, the present invention provides an operation sequence in which aerosolization begins at a predetermined point within the exhalation phase and stops within that exhalation phase, or, alternatively, begins at a predetermined point within an exhalation phase and stops at a predetermined point in the succeeding inhalation phase.

Embodiments of the invention also provide for selection of a particular operating sequence from a plurality of available operating sequences. Similarly, the present invention provides for modes of operation, which modes may include one or more operating sequences.

Embodiments additionally provide for algorithms to set forth operation sequences, choice of operation sequences or choice of modes of operation.

Embodiments also provide for consideration of the identity of a drug to be administered in executing an algorithm, choosing a mode of operation, or selecting or running an operation sequence.

Embodiments of the invention also provide for nebulization of particular drug groups or drugs, such as, for example, antibodies, such as IgG or antibiotics, such as aminoglycosides, such as amikacin.

Embodiments still further provide for a nebulized droplet ejection device for use with a ventilator, wherein the device produces droplets by a vibratory apertured element during a selected interval of a breathing cycle.

Embodiments additionally provide for apparatus and methods for varying the particle size distribution of a nebulized mist by varying the aperture exit diameter of an apertured vibratory aerosolization element.

Additional embodiments and features are set forth in part in the description that follows, and in part will become apparent to those skilled in the art upon examination of the specification or may be learned by the practice of the invention. The features and advantages of the invention may be realized and attained by means of the instrumentalities, combinations, and methods described in the specification.

BRIEF DESCRIPTION OF THE DRAWINGS

FIG. 13 illustrates a simplified method of the present invention;

FIG. 14 is a schematic representation of algorithms of operating sequences in accordance with the present invention;

FIG. 17 is a schematic representation of an algorithm by which an operating sequence may be chosen base on the combination of a plurality of independent sets of information.

DETAILED DESCRIPTION OF THE INVENTION

Overview

As noted above, conventional nebulizer-ventilator systems have low medicament delivery efficiency (e.g., less than 20%). Embodiments of the invention include methods and systems for increasing delivery efficiencies to at least 40%, and in many instances to about 70% or more. The increased efficiency for delivering the aerosolized medicament may be attributable, in part, to one or more features that may be implemented in embodiments of the invention. These features include synchronizing the generation of aerosol with an inspiratory phase of the ventilator cycle (e.g., phasic delivery). The features may also include supplying air (e.g., an "air chaser") following aerosol generation, which can clear the endotracheal tube and reduce the amount of medicament exhaled by the patient. Features may further include connecting the aerosol generating unit directly to the hub of the endotrcheal tube that is connected to the patient. Still other features include generating aerosolized medicament with smaller particle sizes (e.g., about 1 to 5 μm average diameter). Additional features may also include storing the medicament in a conical shaped reservoir to minimize the residual medicament volume.

Embodiments of the systems are configurable to administer aerosolized medicament to a patient both on-ventilator and off-ventilator. On-ventilator treatment methods include administering the nebulized aerosol through a ventilator circuit to the patient. Aerosol doses, containing about 1 to about 500 mg of a medicament, may be delivered through the ventilator circuit in a phasic or non-phasic manner. Off-ventilator treatment methods may include taking the patient off the ventilator before administering the nebulized aerosol. Once the treatment session is completed the patient may be put back on the ventilator, or may breathe on his or her own without assistance.

Embodiments of the invention provide treatments for a variety of ailments using a variety of aerosolizable medicaments. The ailments may include pulmonary ailments such as ventilator-associated pneumonia, hospital-acquired pneumonia, cystic fibrosis, mycobacterial infection, bronchitis, staph infection, fungal infections, viral infections, protozal infections, and acute exacerbation of Chronic Obstructive Pulmonary Disease, among others. The aerosolizable medicaments used to treat the ailments may include antibiotics, anti-oxidants, bronchodialators, corticosteroids, leukotrienes, protease inhibitors, and surfactants, among other medicaments.

Exemplary Pulmonary Drug Delivery Systems

Figure 1A:
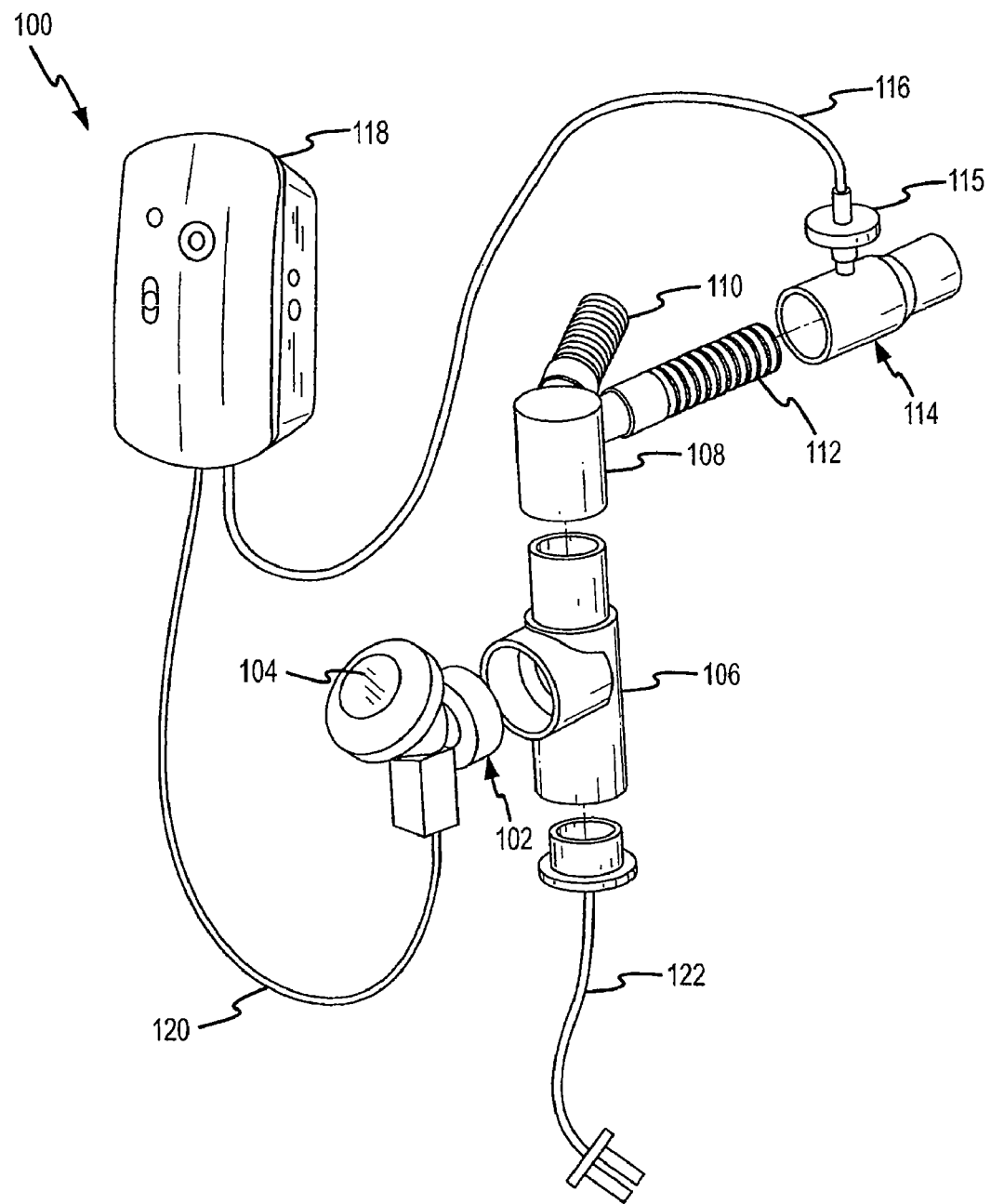
FIG. 1A illustrates components of a pulmonary drug delivery system according to embodiments of the invention.

FIG. 1A shows an embodiment of a pulmonary drug delivery system ("PDDS") 100 according to the invention. The PDDS 100 may include a nebulizer 102 (also called an aerosolizer), which aerosolizes a liquid medicament stored in reservoir 104. The aerosol exiting nebulizer 102 may first enter the T-adaptor 106 that couples the nebulizer 102 to the ventilator circuit. The T-adaptor 106 is also coupled to the circuit wye 108 that has branching ventilator limbs 110 and 112.

Coupled to one of the ventilator limbs 110 or 112 may be an air pressure feedback unit 114, which equalizes the pressure in the limb with the air pressure feedback tubing 116 connected to the control module 118. In the embodiment shown, feedback unit 114 has a female connection end (e.g., an ISO 22 mm female fitting) operable to receive ventilator limb 112, and a male connection end (e.g., an ISO 22 mm male fitting) facing opposite, and operable to be inserted into the ventilator. The feedback unit may also be operable to receive a filter 115 that can trap particulates and bacteria attempting to travel between the ventilator circuit and tubing 116.

The control module 118 may monitor the pressure in the ventilator limb via tubing 116, and use the information to control the nebulizer 102 through system cable 120. In other embodiments (not shown) the control module 118 may control aerosol generation by transmitting wireless signals to a wireless control module on the nebulizer 102.

During the inhalation phase of the patient's breathing cycle, aerosolized medicament entering T-adaptor 106 may be mixed with the respiratory gases from the inspiratory ventilator limb 112 flowing to the patient's nose and/or lungs. In the embodiment shown, the aerosol and respiratory gases flow through nose piece 122 and into the nasal passages of the patient's respiratory tract.

Figure 1B:
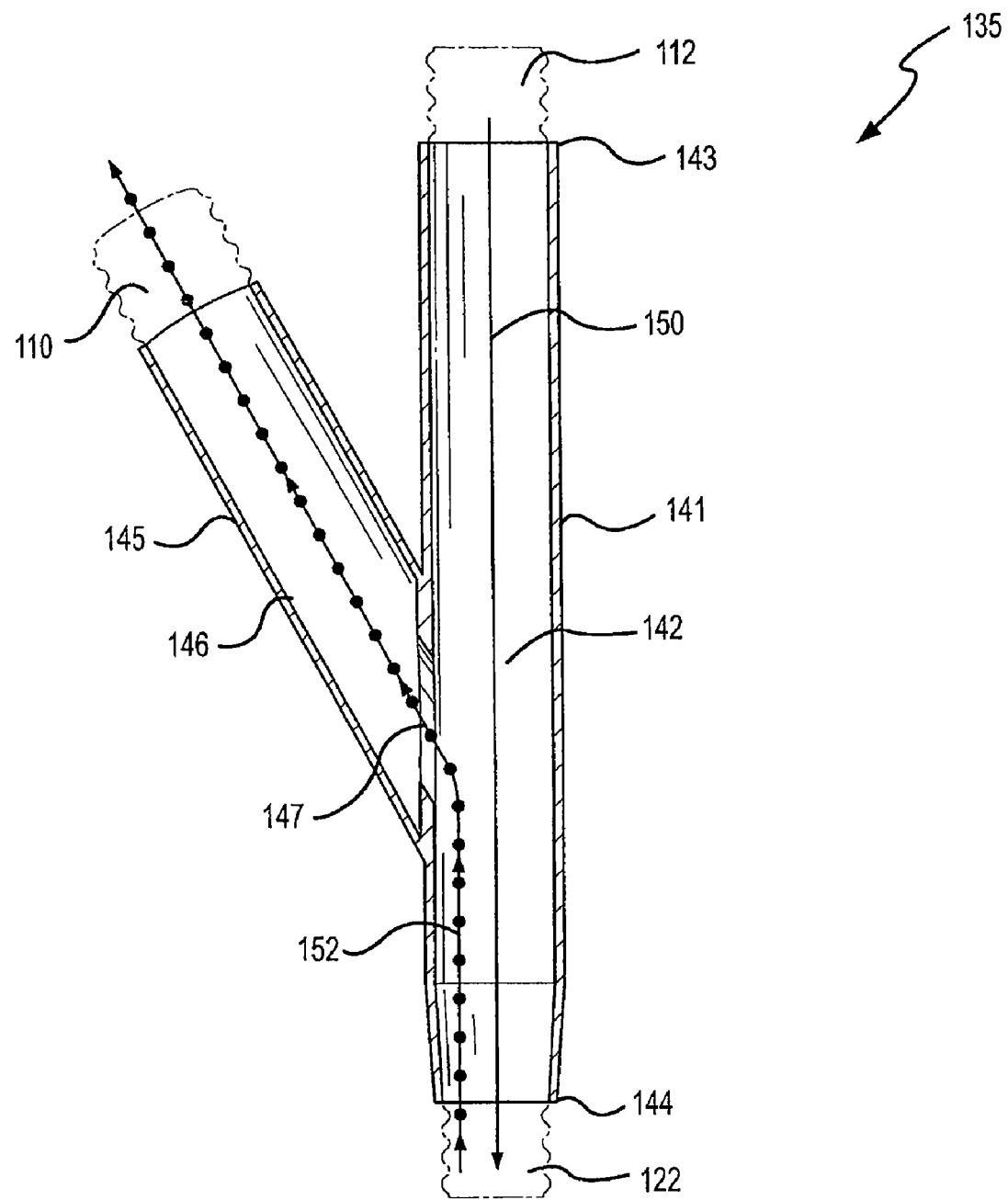
FIG. 1B shows an embodiment of a junction device that can be used in a pulmonary drug delivery system according to embodiments of the invention.

Other embodiments of the circuit wye 108 shown in FIG. 1A are also contemplated in embodiments of the invention. For example, an alternate embodiment of the wye 108 is illustrated in FIG. 1B, which shows junction device 135, which may be configured downstream from nebulizer 102. In the downstream configuration, gas flow 150 containing aerosolized medicament enters the junction device 135 at first end 143 and exits at second end 144 of the respiratory circuit. The junction device 135 includes a tubular main body member 141 having a straight longitudinal lumen 142 connecting the opening in a first end 143 attachable to inspiratory tube 112 and an opening in a second end 144 attachable to a patient interface, such as nose piece 122. Junction device 135 may further comprise a tubular branch member 145 having a lumen 146 that communicates with lumen 142 at intermediate opening 147. Gas flow 150 contains aerosol particles of medicament emitted by nebulizer 102 that pass from inspiratory tube 112 into lumen 142 through the opening in first end 143.

In contrast to a "Y"-shaped junction device, junction device 135 provides for gas flow 150 (containing aerosolized medicament) to follow a straight unobstructed path through the respiratory circuit without any portion being diverted into branch member 145. In other words, there is virtually no change in the angle of the path of gas flow 150. As a result, the full amount of aerosol particles of medicament contained in gas flow 150 is efficiently delivered through the respiratory circuit to the patient. Upon expiratory effort by the patient, expiratory gas flow 152 follows a path through lumen 142 to lumen 146 of branch member 145 and through expiratory tube 110 back to the ventilator (not shown).

Figure 2:
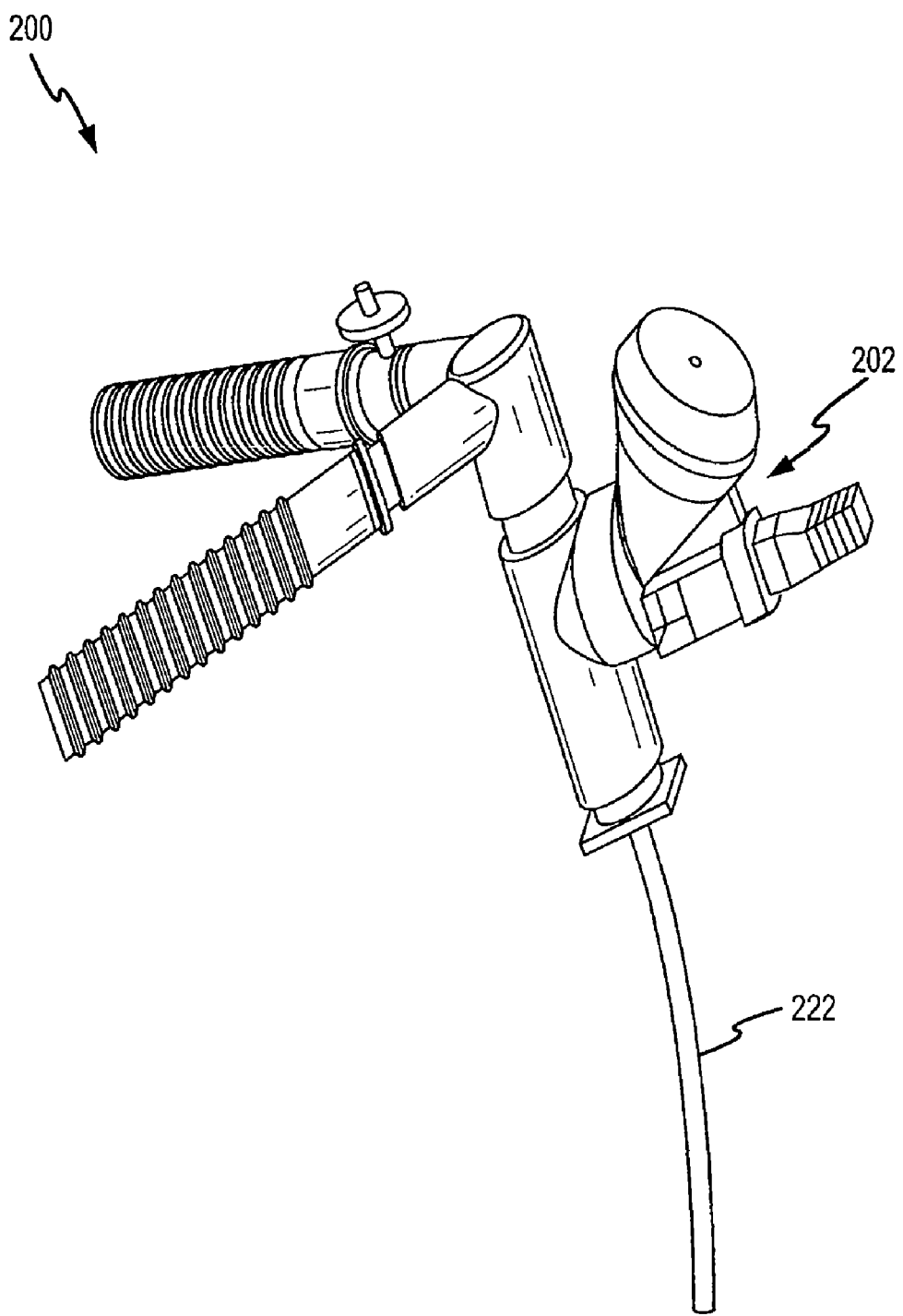
FIG. 2 shows an on-ventilator configuration of a pulmonary drug delivery system according to embodiments of the invention.

FIG. 2 shows another embodiment of a PDDS 200, where nose piece 122 has been replaced by ET tube 222. In this embodiment, during inhalation the aerosolized medicament generated by nebulizer 202 is carried by the flow of respiratory gases through the ET tube 222 and into the patient's bronchial passages and lungs.

Figure 3:
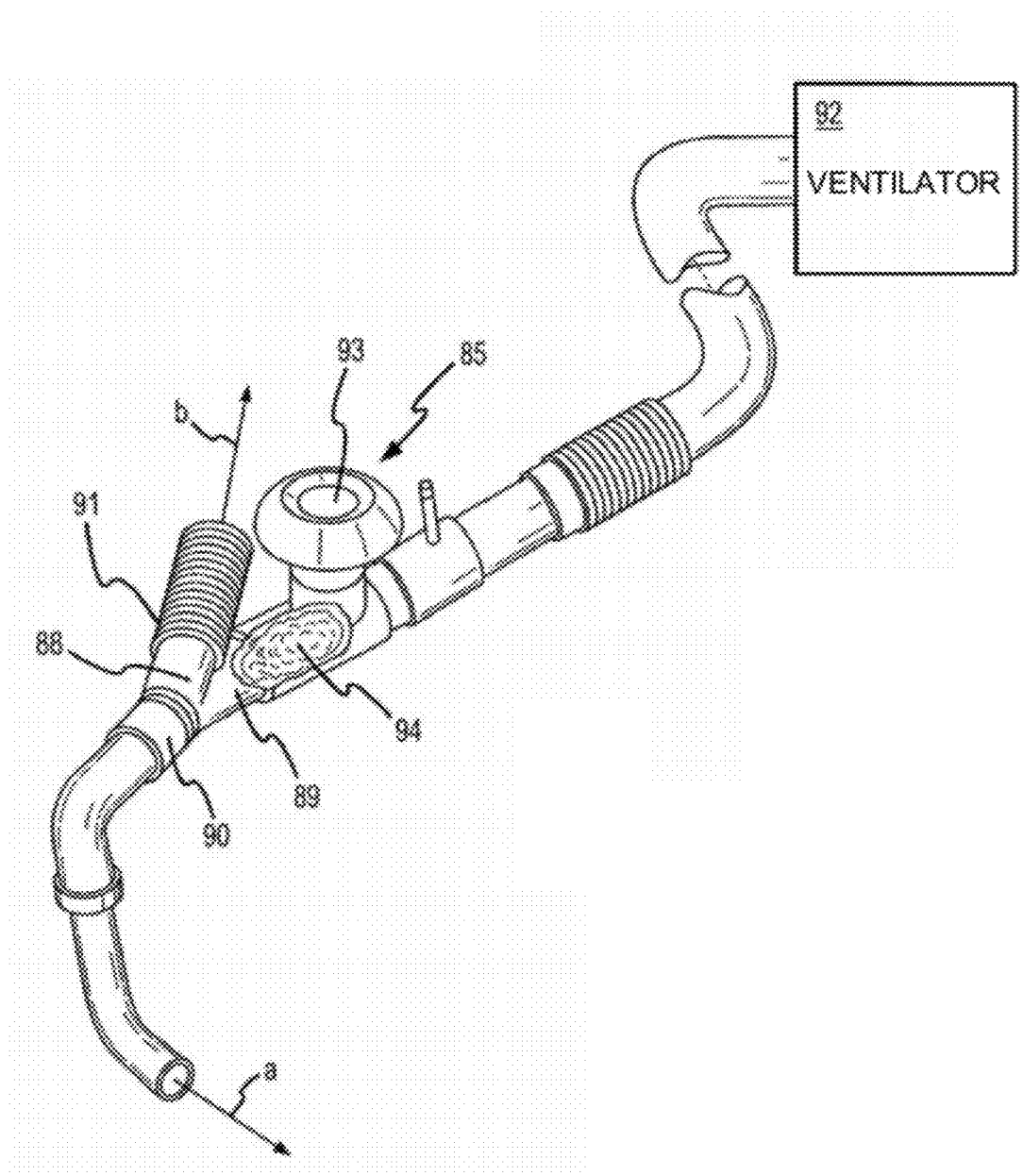
FIG. 3 is a schematic perspective view of a nebulizer incorporated into a ventilator breathing circuit in accordance with the present invention.

Referring to FIG. 3, a nebulizer 85, which may have a top portion 93 through which liquid may be provided may be incorporated into a ventilator breathing circuit of a ventilated patient. The breathing circuit may comprise a "Y" connector 88, which may in turn have an inlet portion 89, an endotracheal tube portion 90 and an outlet portion 91. The inlet portion 89 carries air provided from the ventilator 92 toward the patient. The endotracheal tube portion 90 of the Y connector 88 carries the incoming air to the patient's respiratory tract; this direction is represented by arrow "a". The endotracheal tube portion 90 also carries the patient's exhalation to the outlet portion 91 of the Y connector 88, and the outlet portion may lead to an exhaust, represented by arrow "b", to remove the patient's exhalation from the system. The nebulizer 85 of the present invention aerosolization element generates an aerosol cloud 94 that remains substantially within the inlet portion 89 of the Y connector 88 when there is no inspiratory air flowing through the inlet portion, by virtue of the aerosolization element, as described above, producing a low velocity mist. In this manner, aerosol that is generated when there is no inhalation air being provided will not be carried out through the outlet portion 91 of the Y connector and lost to the ambient environment. Accordingly, a dose of aerosolized medication may be preloaded, i.e., produced and placed substantially within the inlet portion 89 prior to an inhalation phase being sent by the ventilator 92. In this manner, such medication can be swept into a patient's respiratory system at the very start of the inhalation cycle. This may be of particular benefit in the case of neonatal patients and in other instances in which only the initial blast of inhalation phase will reach the target portion of the respiratory system. In alternate embodiments, the ventilator may generate a continuous bias flow of gas through the ventilator circuit. The bias flow may push some of the aerosolized medicament through the outlet portion 91, but there is still an overall benefit from having the aerosolized medicament preloaded through the ventilator circuit.

PDDS systems like the ones described above in FIGS. 1-3 may include equipment for phasic delivery of aerosolized medicaments. This equipment may include breathing characteristics sensors, which can monitor the breathing characteristics of a patient using the PDDS. The sensors can send breathing characteristic information to the PDDS controller to allow the controller to select an appropriate delivery cycle of the aerosolized liquid to the patient. Typically, breathing characteristic sensors can be used to measure a breathing pattern of the patient, the peak flow, breathing rate, exhalation parameters, regularity of breathing, and the like. Such measured breathing characteristics data be delivered to controller by analog or digital signals, and run through a software algorithm to determine an appropriate sequence of delivery relative to the measured breathing cycle to the patient.

For example, one exemplary breathing characteristic that may be sensed by a sensor is the cycle of a ventilator providing air to a patient; for example, the start of an inhalation cycle generated by the ventilator. The sensor may also sense other parameters, for example, it may be an acoustic sensor that is activated through passing the respiratory flow of the patient through an acoustic chamber so as to produce an acoustic tone, which is proportional to the inspiratory flow rate. The frequency of the acoustic tone indicates the inspiratory flow rate at any instant of the breathing cycle. The acoustic signal can be detected by the controller such that integration of the flow rate with time produces the tidal volume. Both the flow rate and the tidal volume can then be used by the controller to determine when the aerosol generator generates the droplets and at what mass flow rate such that maximum deposition of droplets is obtained. Further, the acoustic tone may be recorded to produce a record of the breathing pattern of the patient which may be stored in the microprocessor. This information can be later used to synchronize the ejection of droplets for the same patient. Such information may also be later employed for other diagnostic purposes. A more complete description of such sensors are described in commonly owned, U.S. Pat. No. 5,758,637, which was previously incorporated by reference.

In some embodiments, the sensors can be used to monitor the breathing characteristics of the patient throughout the delivery regime so as to ensure that the aerosol is efficiently delivered throughout the aerosolization procedure. In such embodiments, the controller can adjust the aerosol delivery based on any measured change in the breathing pattern of the patient during the aerosolization. With this monitoring and adjustment predetermined times for the beginning and ending of aerosolization can be reset based on the actual breathing of the patent. In other embodiments, however, the breathing sensor can be used to determine the breathing cycle of a tidal breath and to choose the appropriate pre-programmed delivery cycle that is stored in the memory of the controller. In other embodiments, the controller may be configured to provide aerosol based on the time. For example, the controller may be configured to start aerosol production at the beginning of an inhalation phase of a breathing cycle and stop at a point at which a predetermined percentage of the inhalation has taken place. Alternatively, the controller may be configured to start aerosolization at a first point at which a first predetermined percentage has taken place, and stop aerosolization at a second point at which a second predetermined percentage of that inhalation has taken place. Alternatively, aerosol may begin during an inhalation phase and end during the subsequent exhalation phase. Alternatively, the controller may be configured to begin aerosol production at a certain point during exhalation and stop during that exhalation or during the subsequent inhalation. Thus, embodiments of the PDDS may include a nebulizer having an aerosol generator and a controller configured to have the controller begin aerosolization during exhalation and stop during that exhalation or in the subsequent inhalation. In still other embodiments, the controller may be configured to begin aerosol production at a start point in the breathing cycle, and continue to generate aerosol for a set period of time regardless of how a patient's breathing cycle varies. At the end of the time period, aerosol generation stops until the next start point is in the breathing cycle. In further embodiments, the controller may be configured to start and stop aerosol production for preprogrammed periods of time that are independent of the patient's breathing cycle.

The controller may be operable to allow for a choice of modes of operation, for example, a mode in which aerosolization begins once a certain breath characteristic is detected, such as a sufficient level of inhalation, and ends when there is no longer a sufficient level; another mode in which aerosolization begins once a certain breath characteristic is detected, such as a sufficient level of inhalation, and ends at a predetermined time within the inhalation cycle, such as for example, before the level of inhalation falls below that required for operation of an aerosolization element, or, alternatively, at any other point within the inhalation cycle, such as after the inhalation phase of the cycle before exhalation has begun, or after exhalation has begun.

The level of inhalation may be sensed by a pressure sensor. Such a transducer may monitor a drop in air pressure or a rise in air pressure within a chamber that is in fluid communication with the ventilator circuit. In this manner, a pressure drop may be sensed by a patient inhaling through the circuit, for example, in an instance in which the ventilator provides assisted ventilation initiated by a patient's commencement of an inhalation. Similarly, a pressure rise may be sensed in an instance in which the ventilator pushes inhalation air to the patient without the patient initiating a breath. Another mode in which the controller may be operable is a mode in which the on/off operation of the aerosol generator is triggered by time, which may be ascertained from an internal clock device, such as a clock built into a microprocessor, or from an external source. Another mode in which the controller may be operable is in which the on/off operation of the aerosol is triggered by the controller receiving an external signal, such as a signal from a ventilator, which can correspond to the point in the ventilator's cycle of that is the start of an inhalation phase in which the ventilator begins to push inspiratory air into the ventilator circuit. The controller may be operable between such modes, including a mode in which the aerosolization begins at a predetermined time in the breathing cycle and ends at a predetermined time in the breathing cycle. The first and second predetermined times in the third mode may be during inhalation. Alternatively, the first and second predetermined times may be during exhalation, or at the first predetermined time may be during exhalation and the second predetermined time may be during subsequent inhalation. These times may correspond to certain percentages of the inhalation phase taking place, or any other points of reference within a breathing cycle.

Alternatively, the first predetermined time and the second predetermined time may be designated as any point within a single breathing cycle, or alternatively, the first predetermined point may be at any point within one breathing cycle and the second predetermined point may be at any point in a subsequent breathing cycle. The controller may make the determination of when to begin, and operate to begin aerosolization, and may make the determination of when to stop aerosolization to stop, and cause aerosolization to stop. The controller may make such determinations and take such actions based on accessing stored algorithms. The controller may receive a signal from the ventilator that establishes a reference point, nonetheless, the controller, by making the determinations an taking the actions based on stored algorithms, and/or information obtained as to the identity of a drug to be administered, may cause aerosol production to begin and/or end independent of the instantaneous position of the ventilator with respect to the ventilator cycle.

Embodiments also include a controller operable to allow for a single mode of operation, where the single mode of operation may be any mode, including but not limited to the modes described above. For example, a mode in which aerosolization begins once a certain breath characteristic is detected, such as a sufficient level of inhalation, and ends when there is no longer a sufficient level. Similarly, the controller may operable in a mode in which aerosolization begins once a certain breath characteristic is detected, such as a sufficient level of inhalation, and ends at a predetermined time within the inhalation before there is no longer a sufficient level or an aerosolization element.

Alternatively, the mode may be a mode in which the aerosolization is commenced based on a signal from the ventilator indicating the attainment of a certain point within the ventilation output cycle or the inhalation cycle of the patient. (The ventilation output cycle of the ventilator may coincide with the inhalation cycle of the patient, such that the ventilation output phase of the ventilator output cycle and the inhalation phase of the inspiratory cycle of the patient occur substantially simultaneously. Such may be the case where a patient is completely passive and the only inhalation that occurs is by generation of air from the ventilator during the output phase of the ventilator cycle). Such point may be during the output phase of the output cycle of the ventilator or during the inhalation phase of the inhalation cycle of the patient. The predetermined point can be chosen to coincide with a certain level of output from the ventilator or at a certain point in time during the ventilator output cycle. Such a predetermined point may be a specific point within the output phase of the ventilator cycle, or, a specific point within the non-output phase of the ventilator cycle, based, for example, on the timing of the previous or succeeding output phase of the ventilator. In another aspect, the present invention provides for a ventilator along with the aerosol generator and controller. In an aspect of the invention, a predetermined time may be based on the timing of a ventilator supplying air to a user. In this manner, the controller may be set to work off of the timing of the ventilator in one mode, while working off the patient's inspiratory effort in another mode, or mode that allows for a combination of the patient's inspiratory effort and the timing of the ventilator, for example, where the ventilator is set to assist the patient by supplying air upon the patient's effort or where the patient has not made a sufficient effort within a predetermined period of time.

Exemplary Off-Ventilator Configurations

Figure 4A:
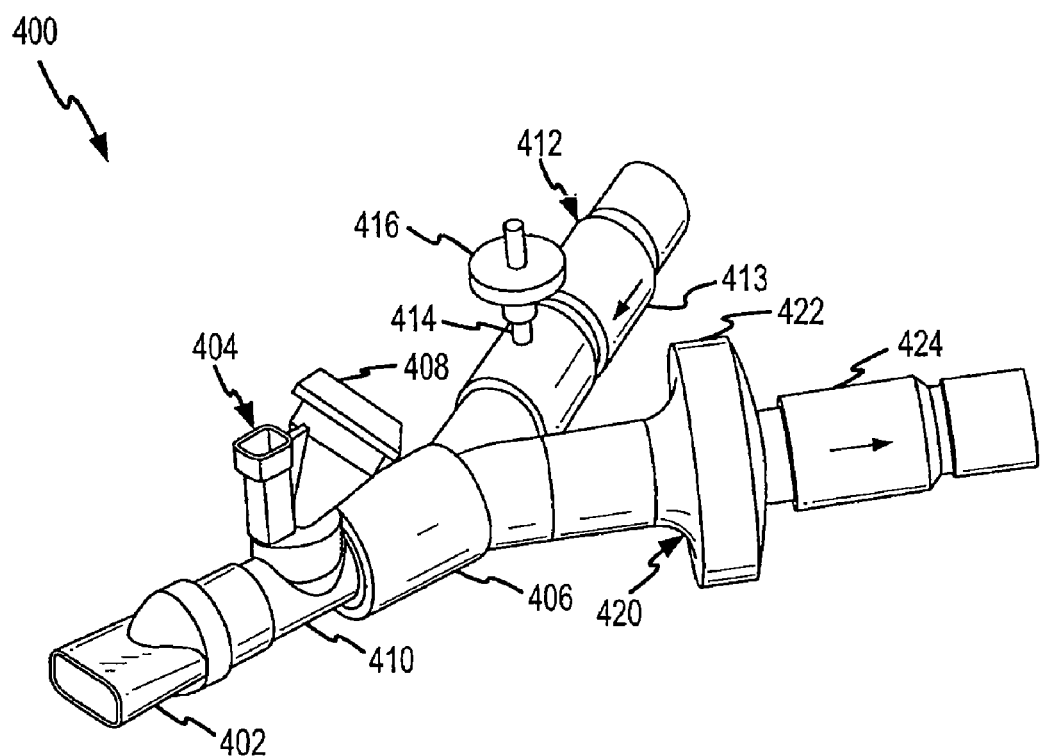
FIGS. 4A-D show off-ventilator configurations of pulmonary drug delivery systems according to embodiments of the invention.

Referring now to FIGS. 4A-D embodiments of off-ventilator configurations of a PDDS are shown. In FIG. 4A, the off-ventilator PDDS 400 includes an endpiece 402 that is coupled to a nebulizer 404 and wye 406. The nebulizer 404 may include reservoir 408, which supplies the liquid medicament that is aerosolized into connector 410. The connector 410 can provide a conduit for the aerosolized medicament and gases to travel from the wye 406 to endpiece 402, and then into the patient's mouth and/or nose. The first wye limb 412 may be connected to a pump or source of pressurized respiratory gases (not shown), which flow through the wye limb 412 to the endpiece 402. A one-way valve 413 may also be placed in the limb 412 to prevent respired gases from flowing back into the pump or gas source. The limb 412 may also include a pressure feedback port 414 that may be connected to a gas pressure feedback unit (not shown). In the embodiment shown, a feedback filter 416 may be coupled between the port 414 and feedback unit.

The off-ventilator PDDS 400 may also include a second wye limb 420, which includes a filter 422 and one-way valve 424, through which gases may pass during an exhalation cycle. The filter 422 may filter out aerosolized medicament and infectious agents exhaled by the patient to prevent these materials from escaping into the surrounding atmosphere. The one-way valve 424 can prevent ambient air from flowing back into the PDDS 400.

Figure 4B:
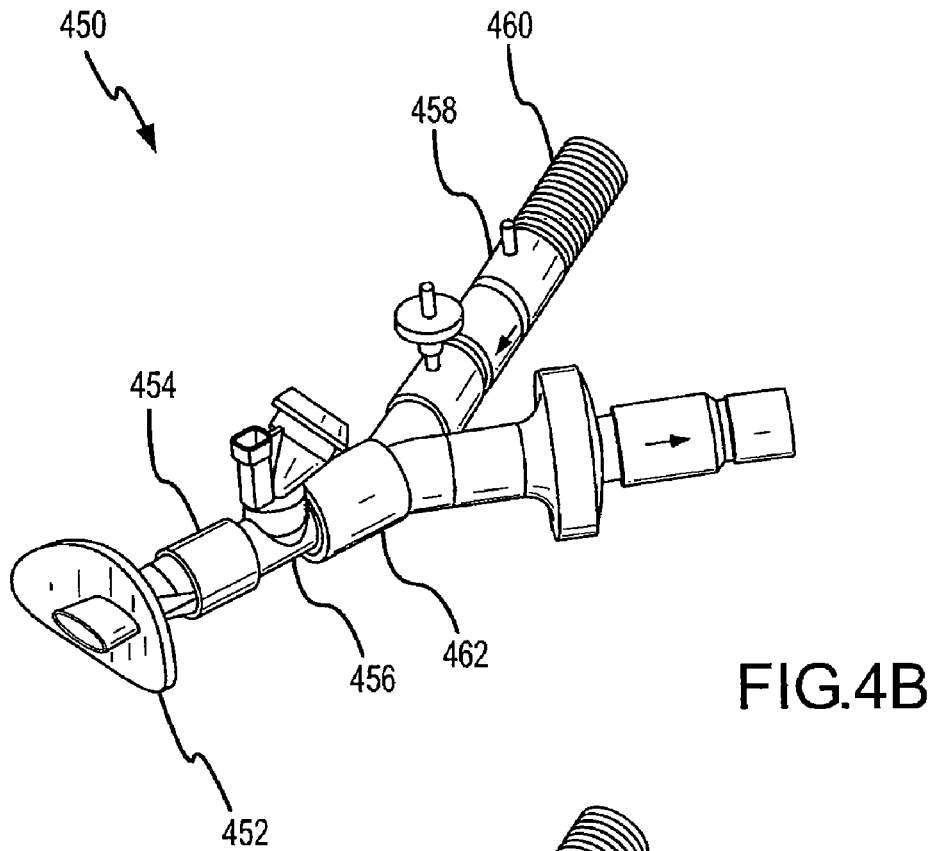

FIG. 4B shows another embodiment of an off-ventilator PDDS 450, where the endpiece is replaced by mouthpiece 452, operable to sealingly engage the lips of a patient. The mouthpiece 452 may be removablely attached to the rest of the off-ventilator PDDS 450 by a connector 454 that is coupled to T-piece 456. The connector 454 may be made from an elastomeric material (e.g., rubber, silocone, etc.) that can resiliently couple the mouthpiece 452 to the T-piece 456. In the embodiment shown, the PDDS 450 also includes a gas inlet port 458 that can be sealingly coupled to an additional gas source (not shown), such as oxygen, on an inspiratory limb 460 of wye 462.

Figure 4C:
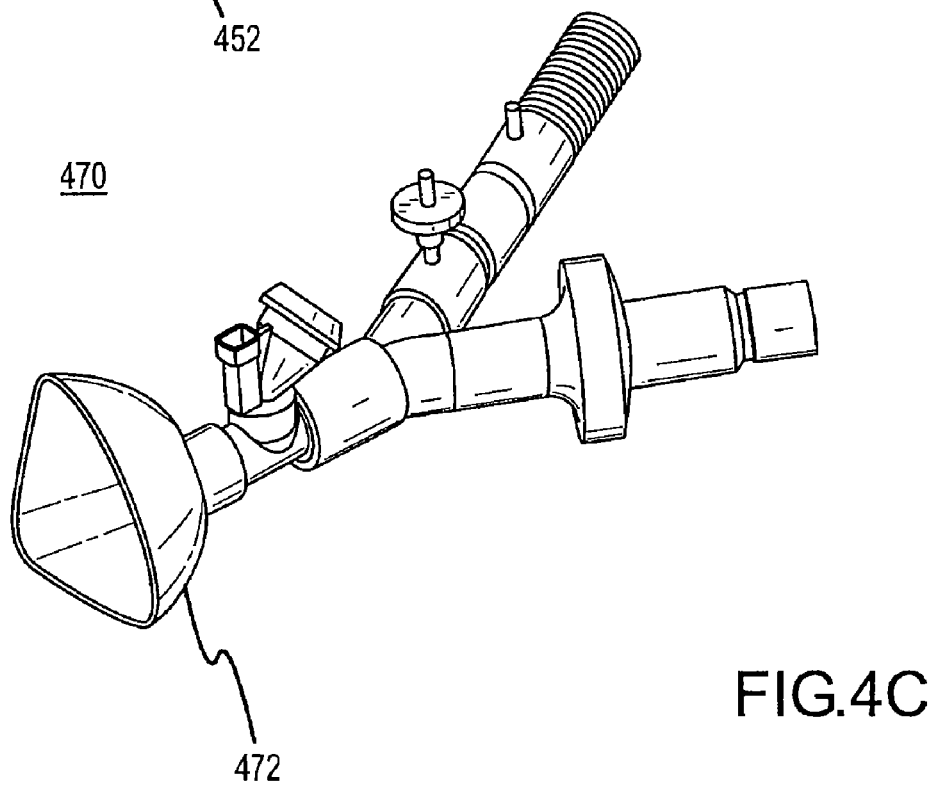

FIG. 4C shows still another embodiment of an off-ventilator PDDS 470, where the endpiece is replaced by a facemask 472, operable to sealingly encompass the nose and mouth of a patient. The facemask 472 may have a coupling end, which can resiliently couple the facemask to the rest of the PDDS 470. The coupling end may be continuous with the rest of facemask 472 to form a single piece.

Figure 4D:
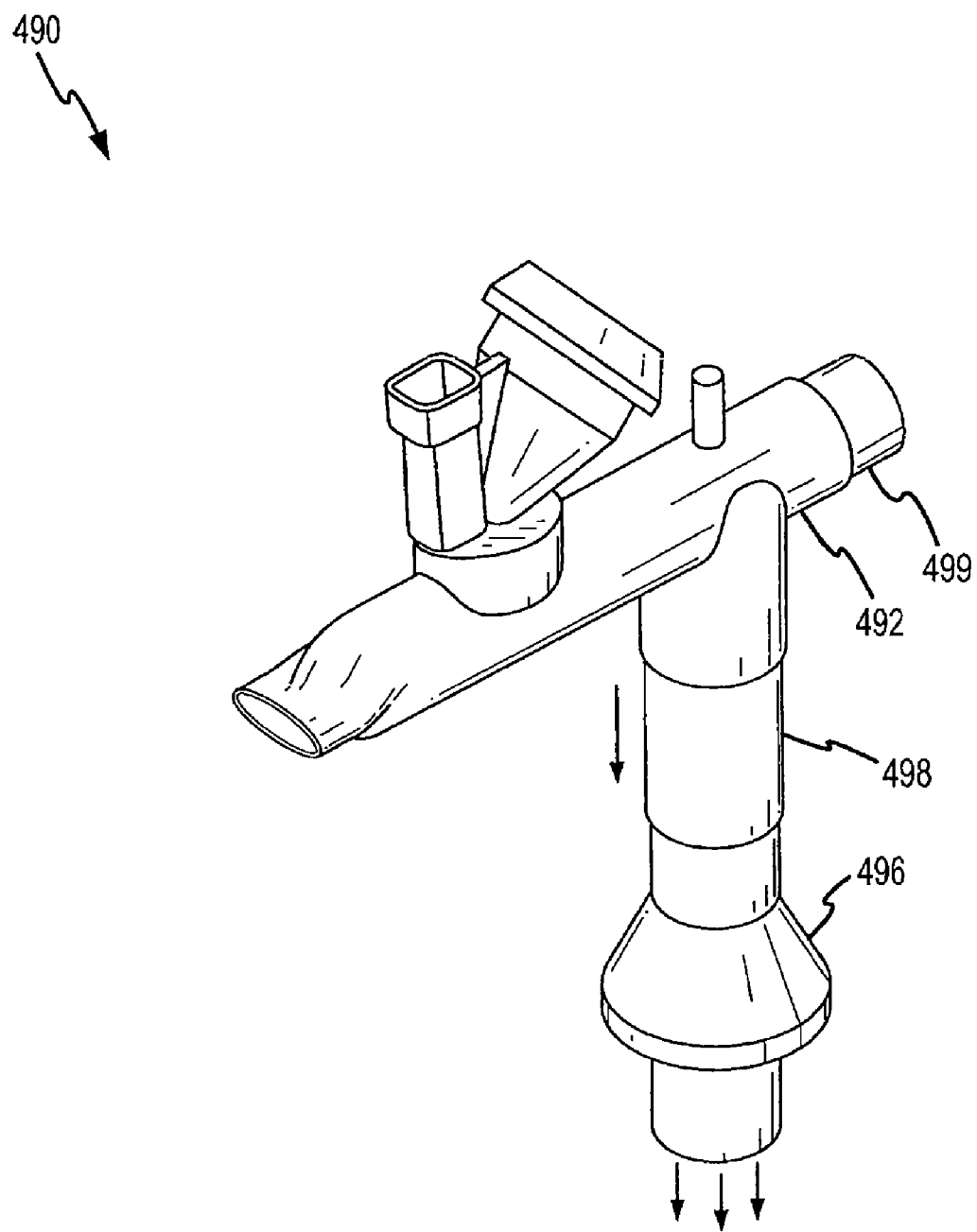

FIG. 4D shows yet another embodiment of an off-ventilator PDDS 490, where the endpiece, T-piece, and wye form a single continuous piece 492. A gas inlet may be contiguously formed in the piece 492 to connect a gas source, such as oxygen. A nebulizer inlet to removably receive a nebulizer may also be formed in piece 492. In addition, a filter 496 and one-way valve 498 may be coupled to a branched end of the piece 492. Another branched end of piece 492 may also be coupled to a one-way valve 499, operable to prevent gases from back flowing into a pump or other pressurized gas source (not shown) coupled to the branched end.

The on and off-ventilator configurations of the PDDS allow continuity of treatment as the patient switches between on-vent and off-vent treatment configurations. In both configurations, a patient is able to receive the same aerosolized medicament at the same dosage level, providing a continuity of treatment as the patient transitions from on-ventilator care to off-ventilator care. This can be particularly useful for extended treatment regimens, when the patient receives the aerosolized medicament for several days or weeks.

Exemplary Nebulizers

In regard to the nebulizers (i.e., aerosol generators), they may be of the type, for example, where a vibratable member is vibrated at ultrasonic frequencies to produce liquid droplets. Some specific, non-limiting examples of technologies for producing fine liquid droplets is by supplying liquid to an aperture plate having a plurality of tapered apertures and vibrating the aperture plate to eject liquid droplets through the apertures. Such techniques are described generally in U.S. Pat. Nos. 5,164,740; 5,938,117; 5,586,550; 5,758,637, 6,014,970, and 6,085,740, the complete disclosures of which are incorporated by reference. However, it should be appreciated that the present invention is not limited for use only with such devices.

Figure 5:
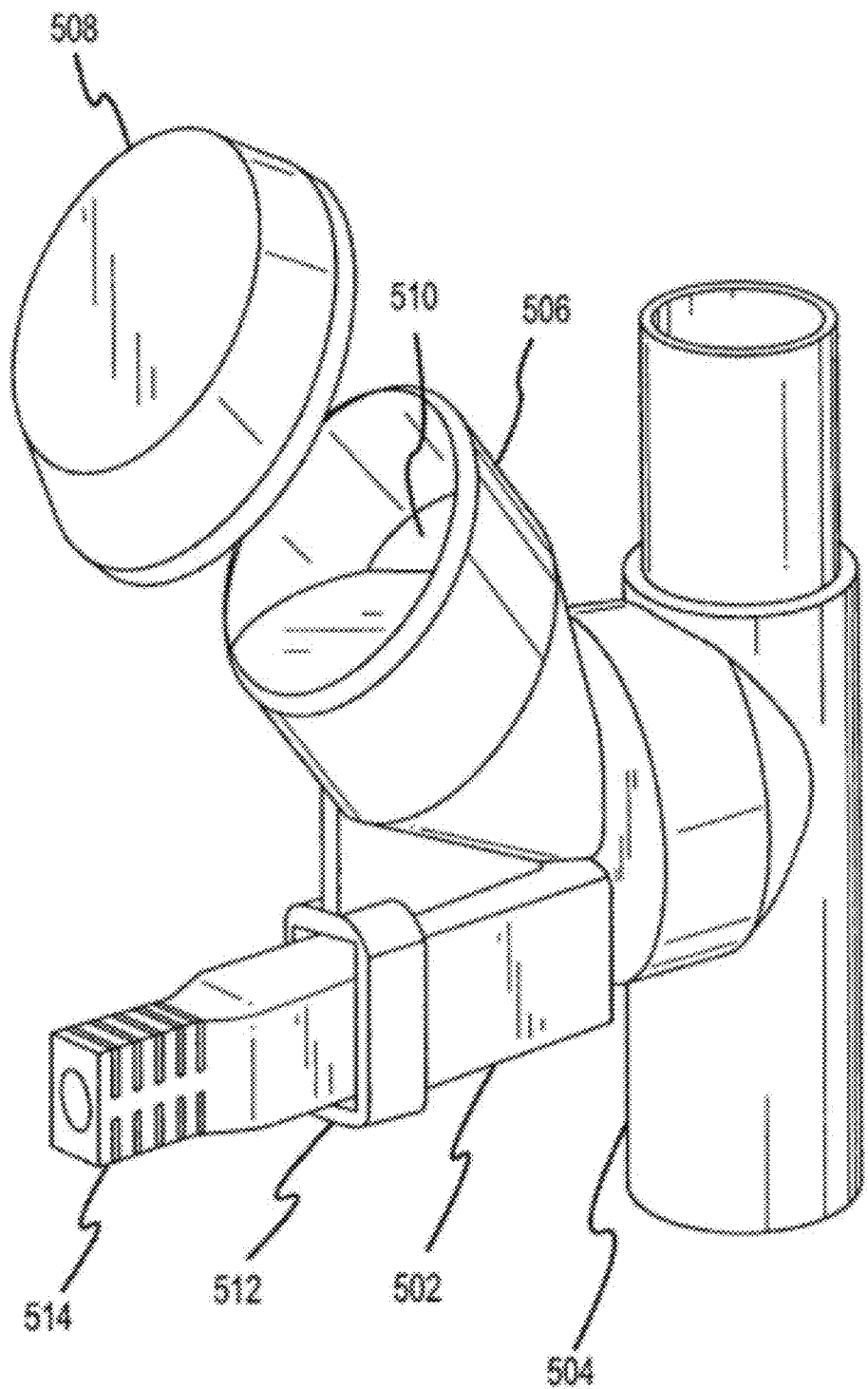
FIG. 5 shows a nebulizer coupled to T-piece adaptor for a ventilator circuit according to embodiments of the invention.

Referring now to FIG. 5, a nebulizer 502 coupled to a T-piece 504 is shown. The nebulizer 502 may include a reservoir 506 that is orientated at a non-perpendicular angle to the T-piece 504. For example, the reservoir 506 may be formed at an angle between about 10° and about 75° with respect to an axis that is collinear with the base conduit of the T-piece 504. The reservoir 506 may have a cap 508 that can sealingly engage an opening in the reservoir 506 to contain a liquid medicament in the reservoir body 510. The cap 508 and top of the reservoir 506 may have conjugate threads or grooves that can be sealingly engaged to close the reservoir. Alternatively, the cap 508 may be made from an elastomeric material that can be elastomerically sealed or snapped into place around the opening in the reservoir 506. The reservoir 506 may be refilled by removing cap 508, adding liquid medicament to the reservoir body 510, and resealing the cap 508 on the reservoir 506. In the embodiment shown, about 4 mL of medicament may be stored in the reservoir body 510. In additional embodiments, the volume of medicament stored may range from about 1 mL to about 10 mL, and larger reservoirs may hold 10 mL or more of a medicament.

The nebulizer 502 may also include a power inlet 512 that can receive a plug 514 that supplies electric power to the nebulizer. Alternatively, the power inlet 512 may be replaced or supplemented by a power cord that terminates with a plug that can be plugged into a power source (not shown). The inlet 512 may also receive an electronic control signal that can control the timing and frequency which the nebulizer aerosolizes medicament from the reservoir 506.

Figure 6:
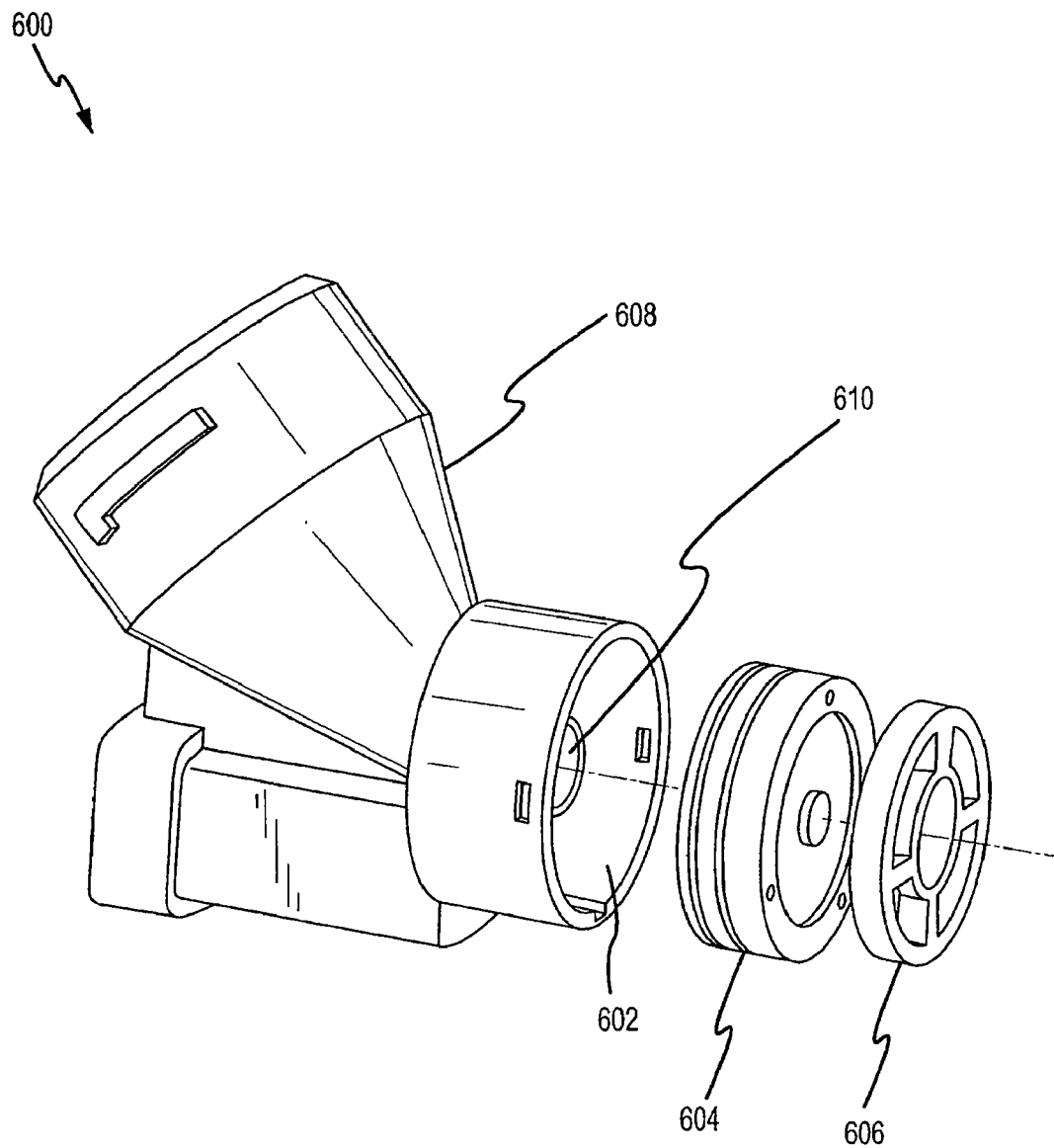
FIG. 6 shows an exploded view of a nebulizer according to embodiments of the invention.

FIG. 6 shows an exploded view of a nebulizer 600 decoupled from the T-piece (not shown), according to an embodiment of the invention. An opening 602 in the nebulizer 600 that couples to the T-piece, or some other inlet in the PDDS, may include an aerosolization element 604 secured within the opening 602 by retaining element 606. In operation, medicament from the reservoir 608 passes through outlet 610 and is aerosolized by the aerosolization element 604. The aerosolized medicament may then drift or flow past retaining element 606 and into the PDDS. Alternative embodiments, not shown, may have the aerosolization element 604 permanently affixed, or integral to, the opening 602, and retaining element 606 may be absent.

The aerosolization element 604 may have a vibratable member that moves with respect to an aperture plate to aerosolized the liquid medicament. By utilizing an aerosol generator that produces aerosol by the electric powering of the vibratable member that causes the aperture plate to eject liquid at one face thereof, through its apertures, as a mist from the other face thereof, as generally described above (and as described generally in U.S. Pat. Nos. 5,164,740; 5,938,117; 5,586,550; 5,758,637, 6,085,740; and 6,235,177, the complete disclosures of which are, and have been above, incorporated herein by reference), the starting and stopping of aerosol generation may be controlled on the level of accuracy of microseconds or milliseconds, thus providing accurate dosing. The timing of aerosol generation can be done based solely on a predetermined timing within a breathing cycle, on timing in conjunction with the length of a prior breath or portions thereof, on other breathing characteristics, on particular medication being administered, or a combination of any of these criteria.

The aerosolization element may be constructed of a variety of materials, comprising metals, which may be electroformed to create apertures as the element is formed, as described, for example, in U.S. Pat. No. 6,235,177 assigned to the present assignee and incorporated by reference herein in its entirety. Palladium is believed to be of particular usefulness in producing an electroformed, multi-apertured aerosolization element, as well as in operation thereof to aerosolize liquids. Other metals that can be used are palladium alloys, such as PdNi, with, for example, 80 percent palladium and 20% nickel. Other metals and materials may be used without departing from the present invention.

Figure 7:
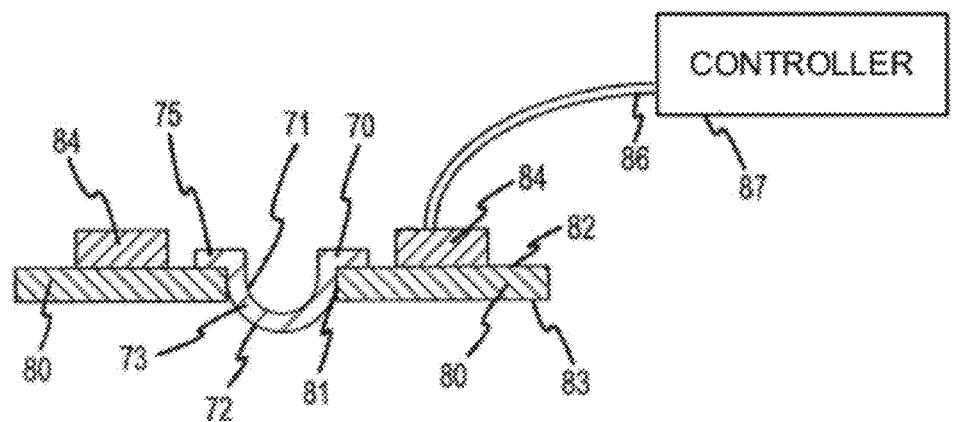
FIG. 7 is a schematic cross-sectional representation of an aerosol generator in accordance with the present invention.
Figure 8:
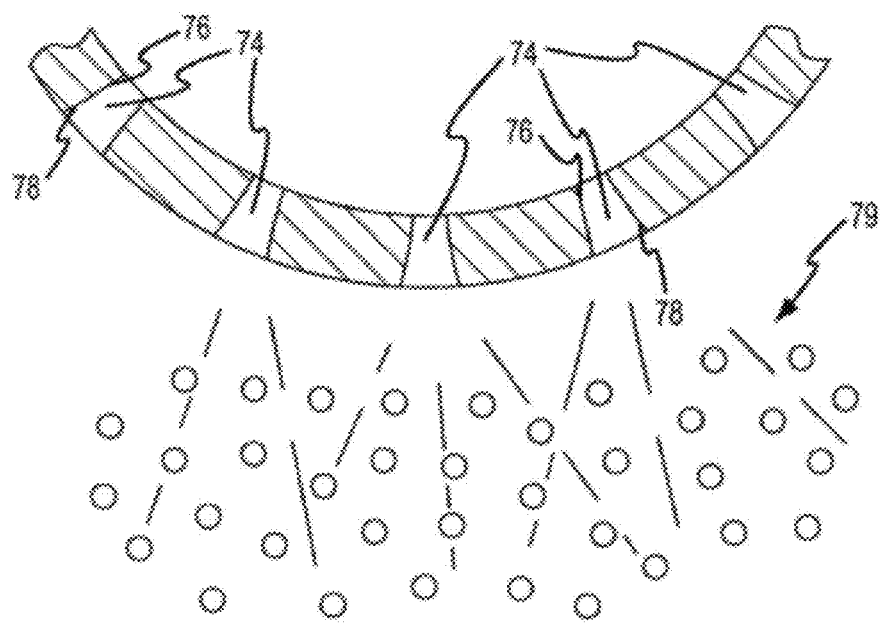
FIG. 8 is a schematic cutaway cross-section detail of the aerosol generator represented in FIG. 6A.

Referring now to FIGS. 7 and 8, an aerosolization element 70 may be configured to have a curvature, as in a dome shape, which may be spherical, parabolic or any other curvature. The aerosolization element may be formed to have a dome portion 73 over its majority, and this may be concentric with the center of the aerosolization element, thus leaving a portion of the aerosolization element that is a substantially planar peripheral ring portion 75. The aerosolization element has a first face 71, a second face 72. As shown in FIG. 8, the aerosolization element may also have a plurality of apertures 74 therethrough. The first face 71 may comprise the concave side of the dome portion 72 and the second face 72 may comprise the convex side of the dome portion 72 of the aerosolization element 70. The apertures may be tapered to have a narrow portion 76 at the first face 71 and a wide portion 78 at the second face 72 of the aerosolization element 70. Typically, a liquid will be placed at the first face of the aerosolization element, where it can be drawn into the narrow portion 76 of the apertures 74 and emitted as an aerosolized mist or cloud 79 from the wide portion 78 of the apertures 74 at the second face 72 of the aerosolization element 70.

The aerosolization element may be mounted on an aerosol actuator 80, which defines an aperture 81 therethrough. This may be done in such a manner that the dome portion of the aerosolization element protrudes through the aperture 81 of the aerosol actuator 80 and the substantially planar peripheral ring portion 75, on the second face 72 of the aerosolization element 70 abuts a first face 82 of the aerosol actuator 80. A vibratory element 84 may be provided, and may be mounted on the first face 82 of the aerosol actuator 80, or alternatively may be mounted on an opposing second face 83 of the aerosol actuator 80. The aerosolization element may be vibrated in such a manner as to draw liquid through the apertures 74 of the aerosolization element 70 from the first face to the second face, where the liquid is expelled from the apertures as a nebulized mist. The aerosolization element may be vibrated by a vibratory element 84, which may be a piezoelectric element. The vibratory element may be mounted to the aerosol actuator, such that vibration of the vibratory element may be mechanically transferred through the aerosol actuator to the aerosolization element. The vibratory element may be annular, and may surround the aperture of the aerosol actuator, for example, in a coaxial arrangement.

Embodiments of the invention include the aerosolization element, or the aerosol generator, comprising the aerosolization element 70, the aerosol actuator 80 and the vibratory element 86 may be replaced with a respective assembly that has apertures of a different size, such as a different exit diameter, to produce a mist having a different aerosol particle size. A circuitry 86 may provide power from a power source. The circuitry may include a switch that may be operable to vibrate the vibratory element and thus the aerosolization element, and aerosolization performed in this manner may be achieved within milliseconds of operation of the switch. The circuitry may include a controller 87, for example, a microprocessor that can provide power to the vibratory element 84 to produce aerosol from the aerosolization element 70 within milliseconds or fractions of milliseconds of a signal to do so. For example, aerosol production may begin within about 0.02 to about 50 milliseconds of such a signal and may stop within about 0.02 to about 50 milliseconds from the cessation of a first signal or a second signal either of which may act as a trigger to turn of aerosolization. Similarly, aerosol production may begin and end within about 0.02 milliseconds to about 20 milliseconds of such respective signaling. Likewise, aerosol production may begin and end within about 0.02 milliseconds to about 2 milliseconds of such respective signaling. Further, this manner of aerosolization provides full aerosolization with a substantially uniform particle size of low velocity mist 79 being produced effectively instantaneously with operation of the switch.

The switch, described above, may be operable by a pressure transducer, which may be positioned in the mouthpiece of the nebulizer. The pressure transducer may be in electrical communication with the circuitry, and a microprocessor may also be in electrical communication with the circuitry, and the microprocessor may interpret electrical signals from the pressure transducer, and may also operate the switch to begin aerosolization. In this manner, nebulization can begin substantially instantaneously with the inhalation of a user upon the mouthpiece. An example of such a sensor switch can be found U.S. application Ser. No. 09/705,063, now abandoned, assigned to the present assignee, the entire content of which is hereby incorporated herein by reference.

Another transducer may be used to sense the absence or presence of liquid in the reservoir, by sensing, for example, a difference between vibration characteristics of the aerosolization element, such as, for example, differences in frequency or amplitude, between wet vibration and substantially dry vibration. In this manner, the circuitry, may, for example by way of the microprocessor, turn the vibration off when there is essentially no more liquid to aerosolize, i.e., when the end of the dose has been achieved, thus minimizing operation of the aerosolization element in a dry state. Likewise, the switch may prevent vibration prior to delivery of a subsequent dose into the reservoir. An example of such a switch is shown in co-assigned U.S. application Ser. No. 09/805,498, now U.S. Pat. No. 6,546,927, the entire content of which is hereby incorporated herein by reference.

Exemplary Nebulizer-Filter Configurations

Figure 9:
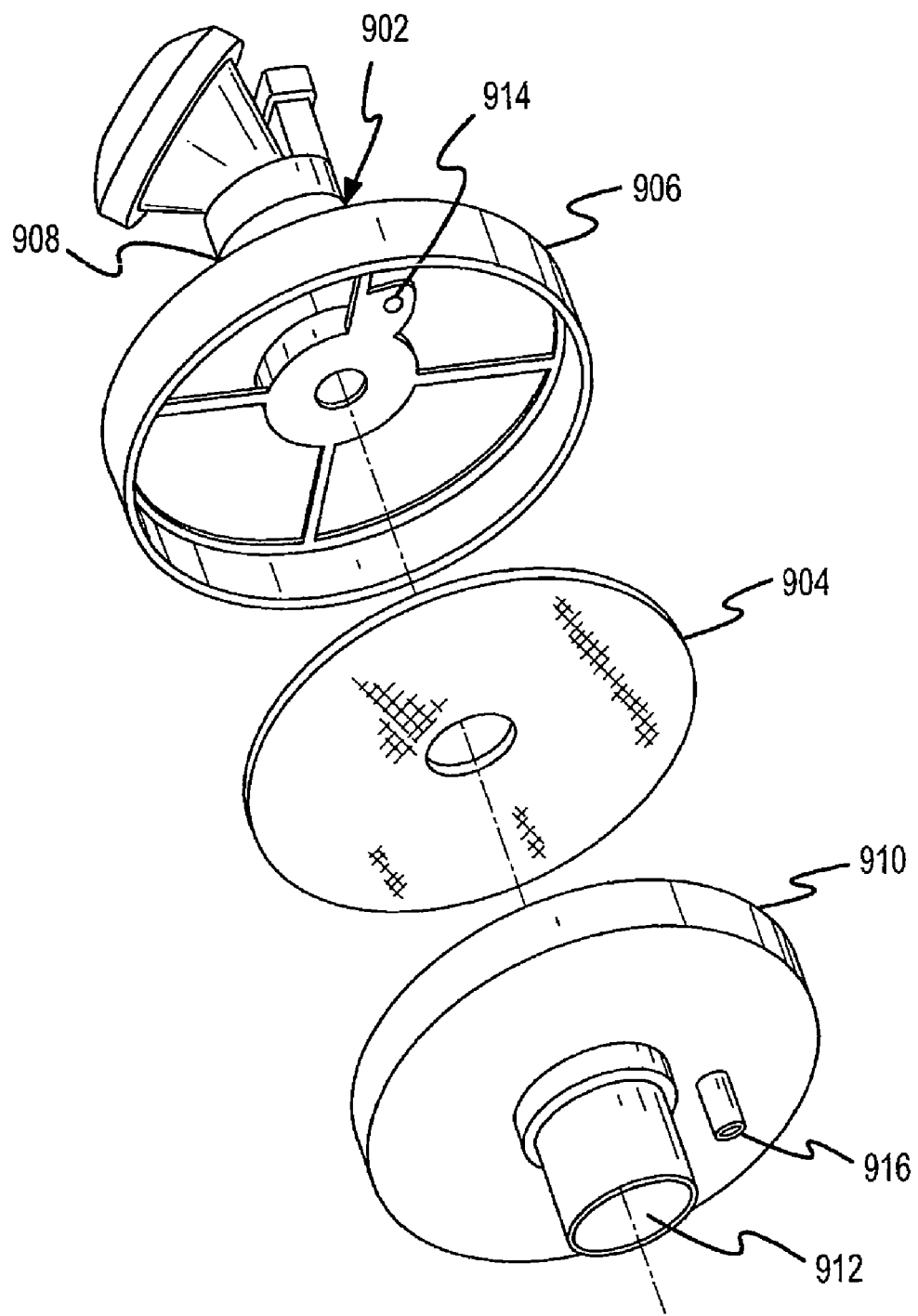
FIG. 9 shows an exploded view of a nebulizer coupled to a filter according to embodiments of the invention.

FIG. 9 shows an exploded view of a nebulizer 902 coupled to a filter 904 according to embodiments of the invention. This configuration of the nebulizer 902 and filter 904 may be part of an off-ventilator apparatus for delivering aerosolized medicament to the patient. The filter 904 may be sandwiched between a first holding element 906, which has a nebulizer port 908 to accept the nebulizer 902, and a second holding element 910, which has a port 912 to accept a mouthpiece, facemask, nose plugs, etc. The first holding element 906 may have one or more openings that permit filtered gases passing through filter 904 to escape into the surrounding environment. Element 906 may also have gas inlet 914 that can sealingly engage with a compressed respiratory gas source (e.g., oxygen, air, etc.) or pump (not shown). The second holding element 910 may have a pressure port 916 that can sealingly engage with a pressure sensor (not shown) that measures the gas pressure in the apparatus.

Figure 10A:
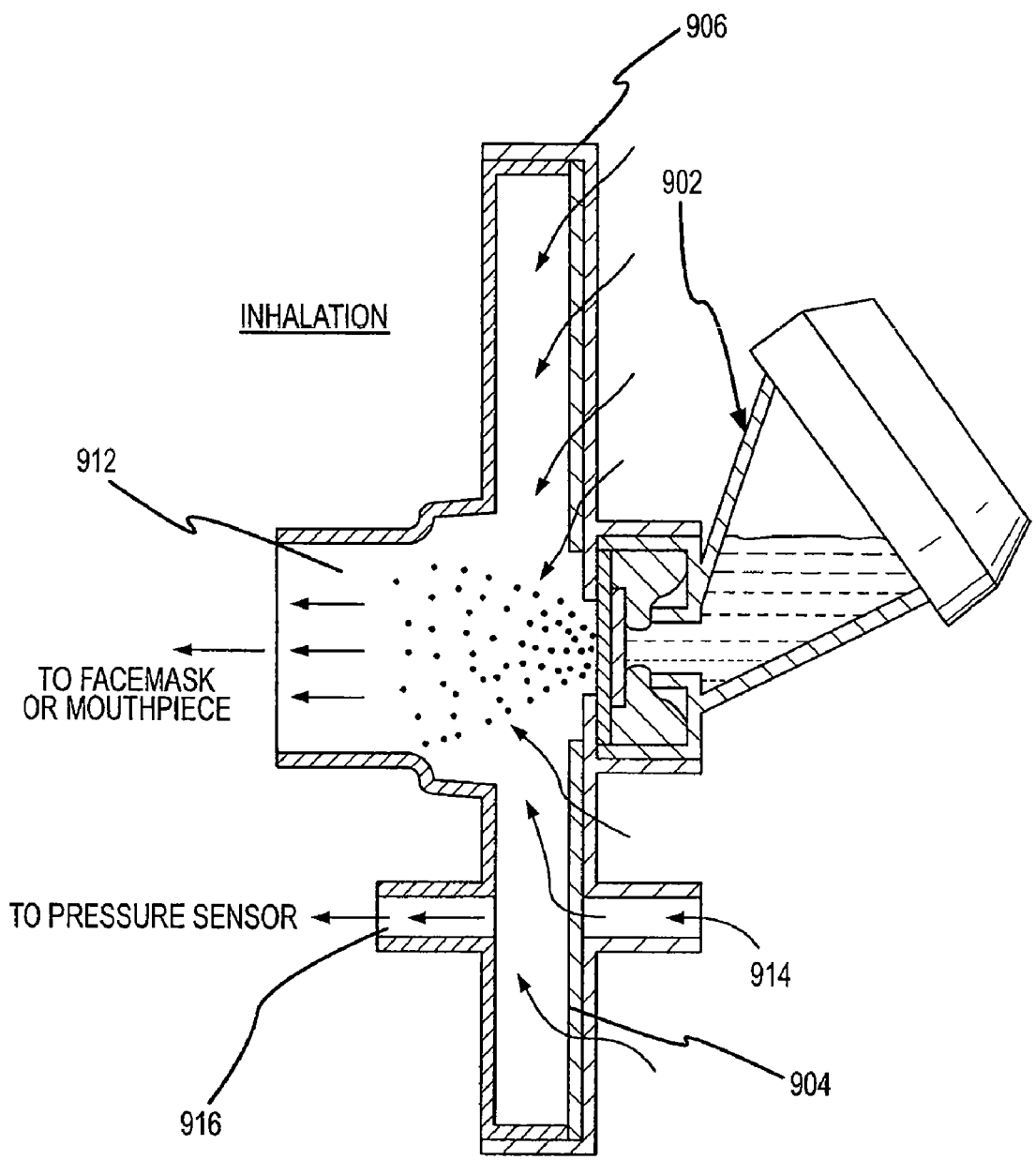
FIGS. 10A-B show the flow of gases and medicaments through a nebulizer-filter system according to embodiments of the invention.
Figure 10B:
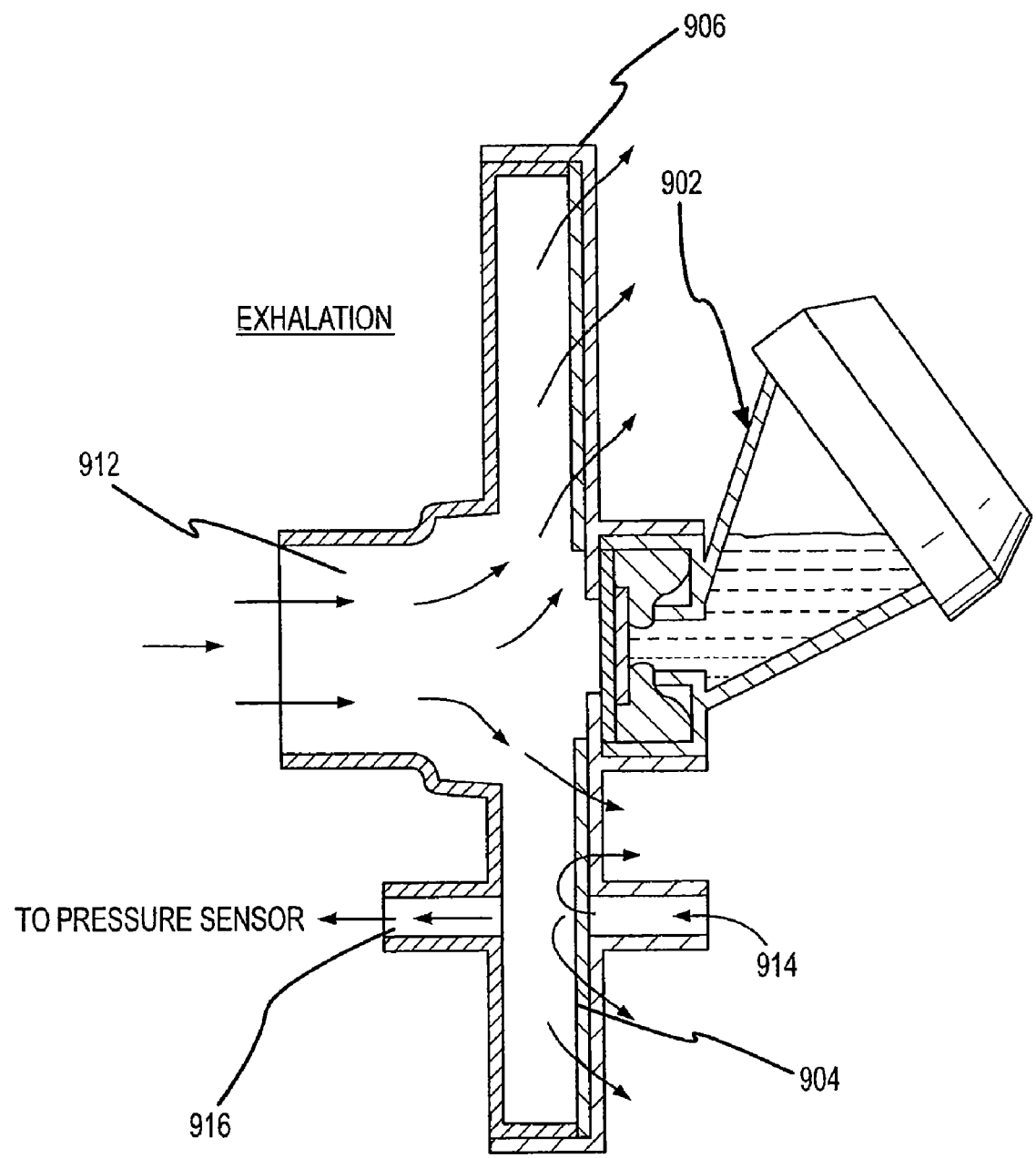

FIGS. 10A-B show the above-described nebulizer-filter configuration in operation during the inhalation (FIG. 10A) and exhalation (FIG. 10B) phases of a patient's breathing cycle. During inhalation, pressurized gas passes through gas inlet 914 and filter 904 into an area where the gases are mixed with aerosolized medicament generated by nebulizer 902. The aerosol and gas mixture then flow through port 912 and into the patient's lungs. In the exhalation phase, gases respired by the patient enter the apparatus through port 912 and exit through the openings in holding element 906 after being filtered through the filter 904.

The pressure in the apparatus may be monitored throughout the breathing cycle with a pressure sensor coupled to pressure port 916. The pressure sensor (not shown) may generate an analog or digital electronic signal containing information about the pressure level in the apparatus. This signal may be used to control the amount of aerosolized medicament and/or gases entering the apparatus over the course of the patient's breathing cycle. For example, when the pressure in the apparatus decreases as the patient inhales, the pressure signal may cause the nebulizer 902 to add aerosolized medicament to the apparatus, and/or cause the gas source or pump to add gas through inlet 914. Then, when the pressure in the apparatus increases as the patient exhales, the pressure signal may cause the nebulizer 902 to stop adding aerosolized medicament to the apparatus, and/or cause the gas source or pump to stop adding gas through inlet 914. Controlling the aerosol and/or gas flow based on the patient's breathing cycle, i.e., phasic delivery of the gases and aerosols, will be described in additional detail below.

Exemplary Aerosol Chamber

Figure 11A:
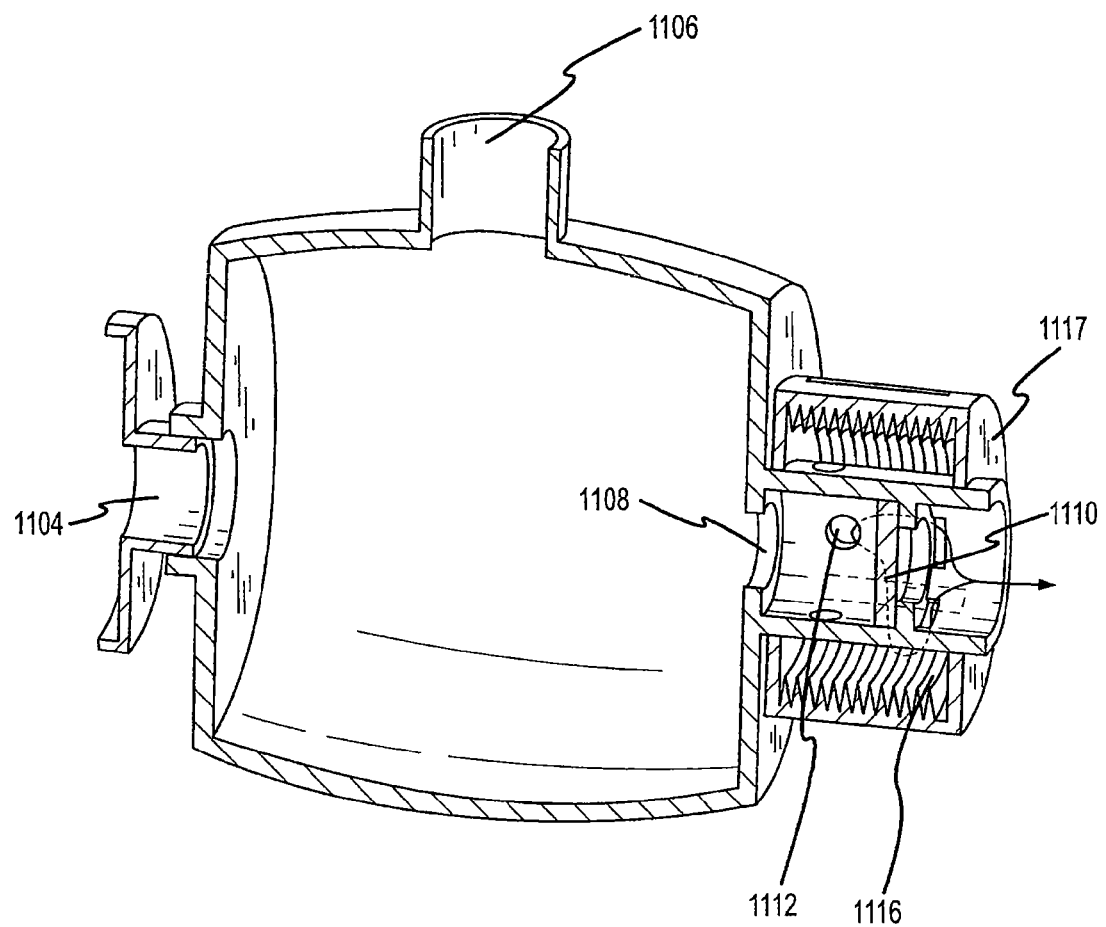
FIGS. 11A-B show the flow of gases through a chamber and filter according to embodiments of the invention.
Figure 11B:
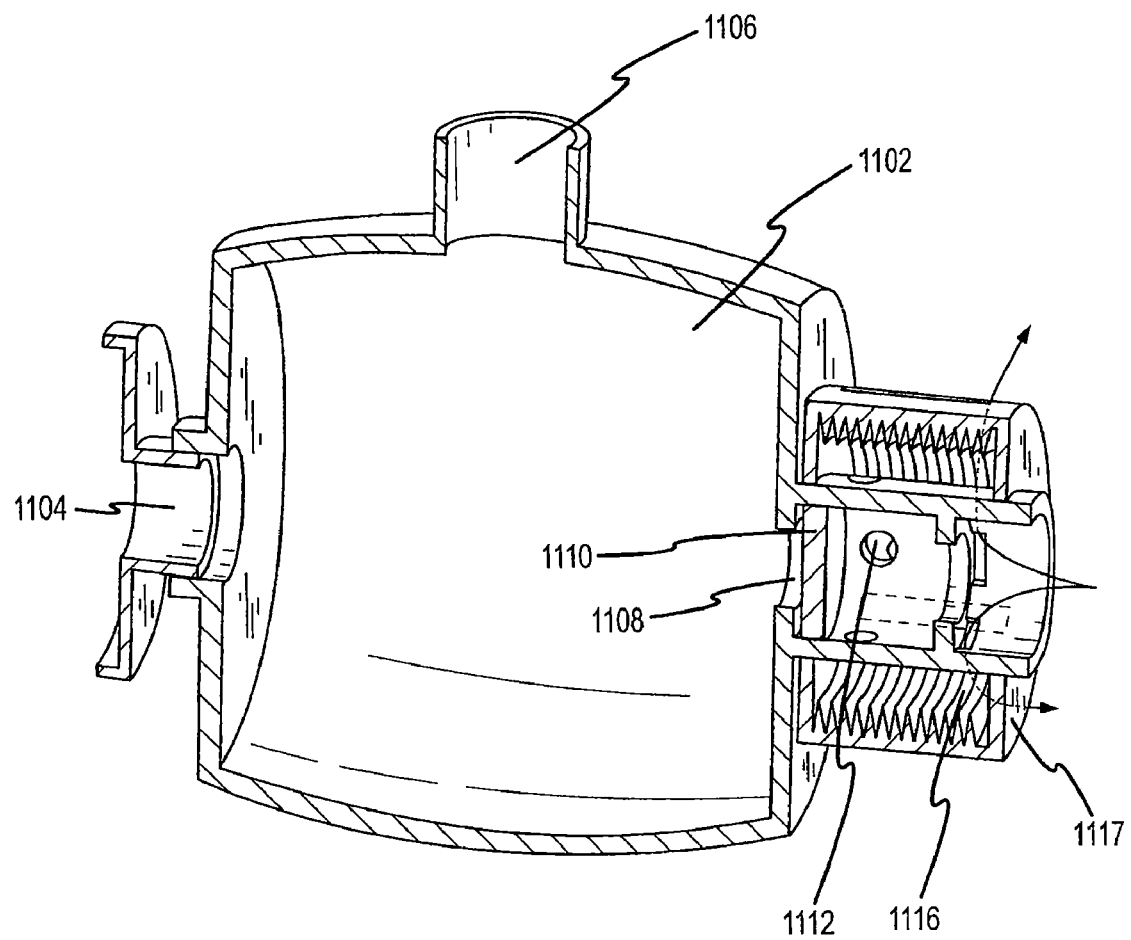

Embodiments of the invention may include a chamber 1102 that can hold gas and aerosol mixtures for delivery to the patient's lungs. The chamber may be used in both on-ventilator and off-ventilator configurations. The expanded volume within the chamber reduces the surface area to volume ratio at the patient interface end of the system, which can increase the aerosol delivery efficiency. FIGS. 11A-B show an embodiment of such a chamber, with flow paths for gases and aerosols being inhaled and exhaled by a patient. The chamber 1102 may include a plurality of ports, including a gas inlet port 1104 that can receive gases from a ventilator, pump, and/or compressed gas source (e.g., a tank of compressed air, oxygen, etc.). The chamber 1102 may also include a second port 1106 that can receive a nebulizer (not shown), and a third port 1108 that can receive an endpiece (e.g., a mouthpiece, facemask, etc.).

Port 1108 may include a valve 1110 that can change the fluid flow path through the port 1108 depending on phase of a patient's breathing cycle. For example, during an inhalation phase (FIG. 11A), valve 1100 may be pushed away from the chamber 1102, channeling the gases and aerosols to flow around the ends of the valve into the endpiece (not shown), and ultimately into the patient's lungs. Then, during an exhalation phase (FIG. 11B), the valve 1110 is pushed by the patient's respiring gases to close port 1108, forcing the gases through openings 1112 and filters 1116 before exiting the filter housing 1117 into the surrounding atmosphere. The filter housing 1117 may include perforations that allow exhaled gases to exit and/or be constructed from gas permeable materials through which exhaled gas may diffuse.

Exemplary Medicaments

Embodiments of the invention contemplate a variety of medicaments that can be aerosolized and delivered to a patient's lungs. These medicaments may include antibiotics such as aminoglycosides, β-lactams, and quinolines, among others. The aminoglycosides may include amikacin, gentamycin, kanamycin, streptomycin, neomycin, netilmicin, and tobramycin, among other aminoglycosides. Other medicaments may also be used, including anti-oxidants, bronchodilators, corticosteroids, leukotrienes, prostacyclins, protease inhibitors, and surfactants, among other medicaments. Table 1 lists classes of medicaments and some of the aliments they may be used to treat in their aerosolized state.

TABLE 1

Classes of Aerosolizable Medicaments

| Medicament Class | Aliments Treated | Dosing | Duration of Treatment |
| --- | --- | --- | --- |
| Anti-oxidants | RDS, Prevention of BPD, ALI, ARDS | 1-4 per day | Duration of ventilation |
| Bronchodilators | Asthma, COPD, ARDS, RDS | 1-4 per day | As needed |
| Corticosteroids | Asthma, COPD, BPD | 1-2 per day | Duration of ventilation |
| Leukotrienes or related agonists | Immunodeficiency, COPD, Treatment/prevention of pneumonia or RSV infection | 1-4 per day | 5-14 days |
| Prostacyclin or related analogues | PPHN, Secondary pulmonary hypertension, Post-cardiac surgery, ARDS | Continuous | TBD |
| Protease inhibitors | AECOPD, ARDS, RDS, BPD | 1-2 per day | 5-14 days |
| Surfactants | RDS, Prevention of BPD, ARDS | 1-2 per day | TBD |

Figure 12A:
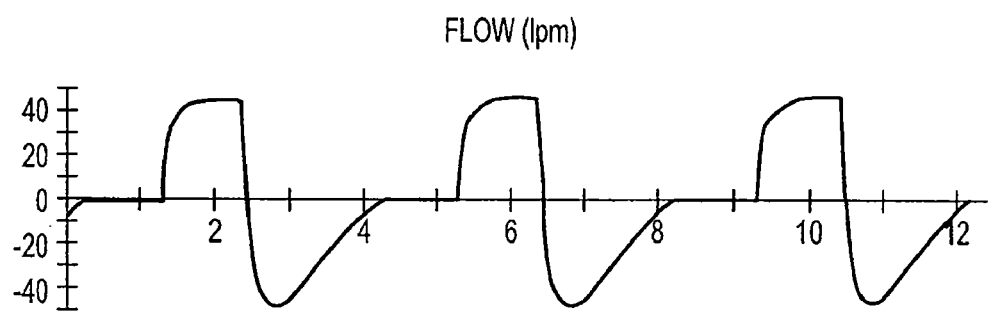
FIGS. 12A-C show graphs of various modes of aerosolization over the course of breathing cycles.
Figure 12B:
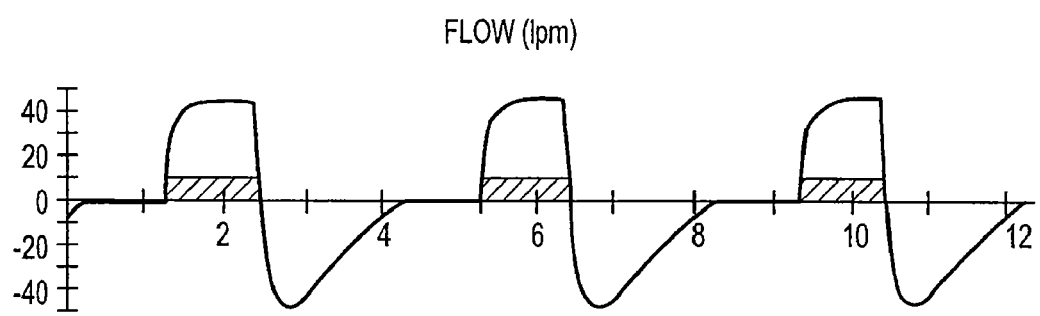
Figure 12C:
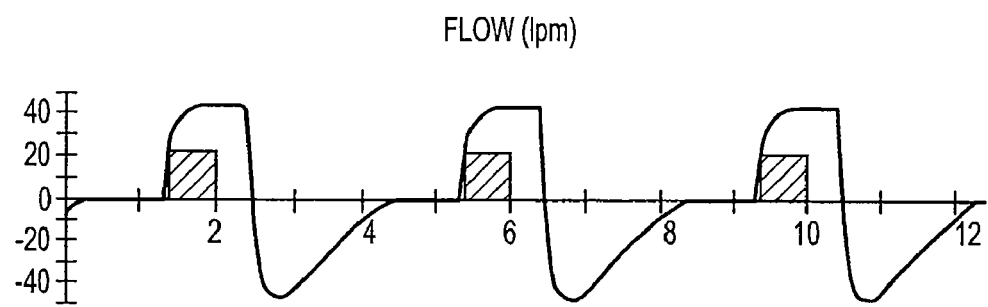
Figure 15:
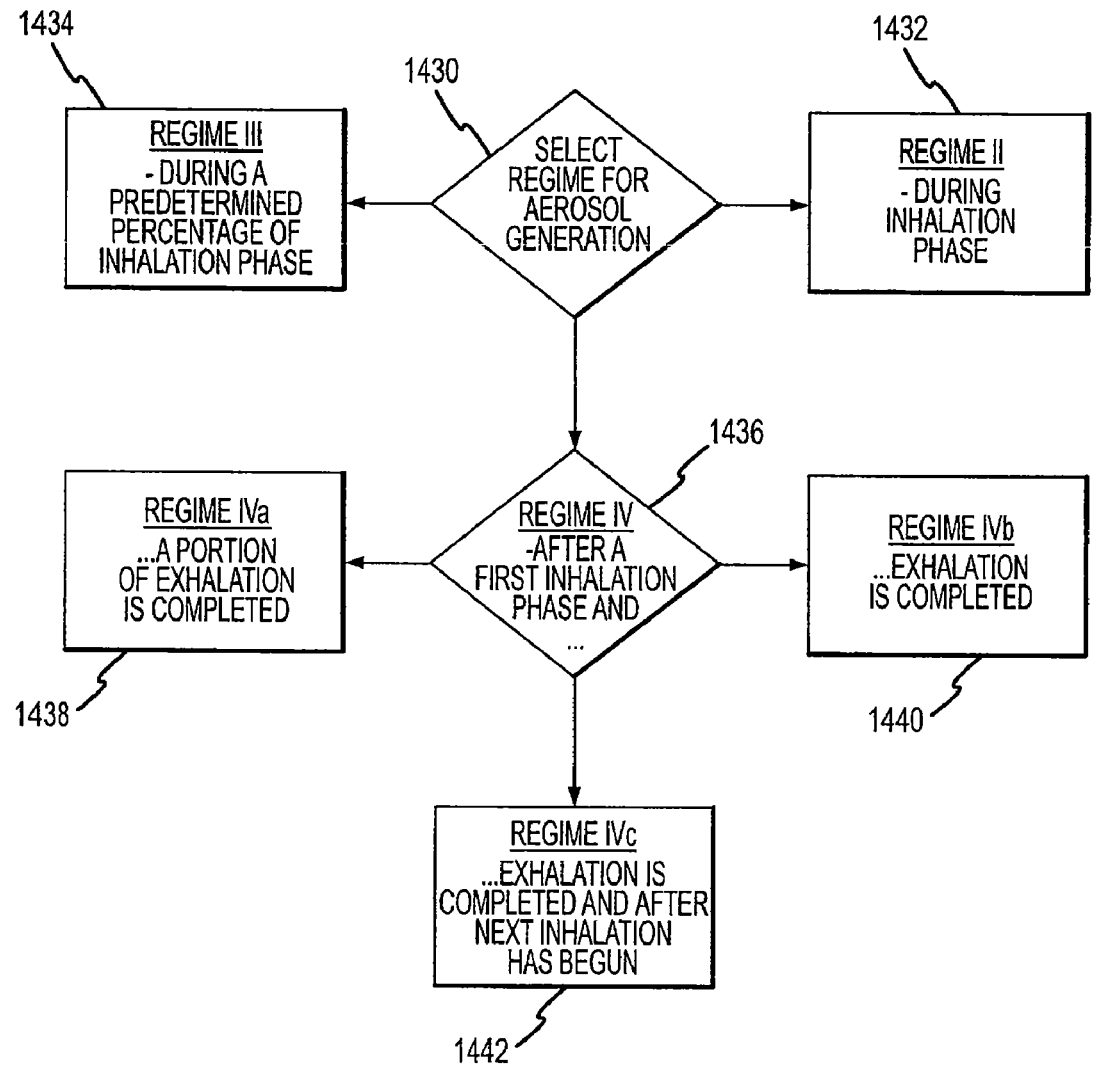
FIG. 15 is an alternative schematic representation of the algorithms of operating sequences of FIG. 14.

AECOPD: acute exacerbation of COPD
ALI: Acute lung injury
ARDS: Acute respiratory distress syndrome
BPD: Bronchopulmonary dysplasia
COPD: chronic obstructive pulmonary disease
PPHN: persistent pulmonary hypertension
RDS: Respiratory distress syndrome (also known as infant respiratory distress syndrome)
RSV: Respiratory syncytial virus Exemplary Phasic Delivery Methods FIGS. 12A-C show graphs of various modes of aerosolization over the course of breathing cycles. FIG. 12A shows a continuous aerosolization mode where aerosolized medicament is generated a constant rate throughout the breathing cycle. Continuous (i.e., aphasic) generation modes typically have about 10% to about 15% aerosol delivery efficiency. FIG. 12B shows a phasic delivery mode where aerosolized medicament is administered for substantially all of the inhalation phase of the breathing cycle. These modes typically have about 15% to about 25% efficiency. FIG. 12C shows another phasic delivery mode where the aerosolized medicament is administered during a predetermined portion of the inhalation phase beginning, for example, at the onset of inhalation. It has been discovered that these modes typically have delivery efficiencies between about 60% to about 80%, by weight, of the total amount of medicament that is aerosolized.

Embodiments of the invention take advantage of this discovery by controlling delivery to a predetermined percentage of the breathing cycle, such as a predetermined percentage of the inhalation phase of the breathing cycle, to provide greater delivery efficiency than either continuous delivery or delivery during the entire inhalation phase. Embodiments of the invention also take advantage of the surprising discovery that the percentage of increase in efficiency in delivery for such a predetermined portion of the inhalation phase over delivery during the entire inhalation phase is itself greater than the increase in efficiency of delivery during the inhalation phase compared to aphasic administration of the aerosol.

Phasic delivery methods may include measuring the characteristics of a patient's inhaled breath, typically a tidal breath, and using the measurements to control the operation of the aerosol generator. FIG. 13 provides a simplified flowchart that illustrates some of the steps for phasic delivery of an aerosolized medicament according to embodiments of the invention. Phasic delivery methods may include having a patient can take one or more breaths 1320, and measuring the characteristics of the breath 1322. The breathing characteristics that can be measured include, but are not limited to, a breathing pattern, peak inspiratory flow rate, breathing rate, exhalation parameters, regularity of breathing, tidal volume, and the like and can estimate a user's tidal volume based on such information.

The user can take another tidal breath and the aerosol generator can be operated based on the measured characteristics of the tidal breath 1324. It should be appreciated however, that instead of a tidal breath, the person can take other types of breath. Alternatively, the controller may base the timing of operation of the aerosol generator so that aerosol is generated at specific time periods within a breathing cycle. For example, the controller may operate the aerosol generator for the first 50 percent of inspiration. Alternatively, the controller may operate the aerosol generator to generate aerosol after a portion of inhalation has taken place and to cease producing aerosol after another portion of inhalation has taken place. For example, the controller may cause aerosol to be generated beginning after 20% of the inspiration has taken place and cause aerosol production to cease after 70% of inspiration has taken place. The controller may cause aerosol production to start after, for example, after 90% of exhalation has taken place and, for example, cause aerosol production to stop after 30% of the following inspiration has taken place. By controlling the specific timing within the breathing cycle that aerosolized medication is provided into the breathing circuit, greater efficiency of drug administration can be achieved.

Since some of the pharmaceuticals to be aerosolized may be more effective when delivered near the beginning of a patient's breathing cycle, while other pharmaceuticals may be more effective when delivered near the end of the patient's breathing cycle, the timing of the aerosol generation depends on the type of medicament delivered. If it is known what type of medication or drug is being delivered, the controller can select the best time during the patient's breathing cycle to deliver the aerosol, based upon a predetermined regimen for that drug that is stored in memory. As an additional benefit, an estimate of the patient's age and/or distress can be made, for example, by measuring the tidal volume and breathing rate. Such measurements can influence the efficiency requirements of the dose per breath. These or other variables can be used in establishing various regimes for aerosol delivery, in particular delivery into the breathing circuit of a ventilator. These regimes can be stored in memory and then accessed by the controller as appropriate for a given patient condition.

For example, for a bronchodilator the best time to delivery may be half way through the inhalation phase of a breath when impaction would be reduced since inhalation flows are reducing. For steroids, it may be best to deliver towards the end of the inhalation phase of a breath. For antibiotics, it may be best to slightly pre-load, e.g., deliver aerosol during the exhalation phase, or deliver right at the start of the breath. For example, antibiotics may be delivered at the beginning of a ventilator provided inhalation, and the aerosol delivery may stop after a predetermined percentage of the inhalation has been provided. One class of antibiotics that may be administered in accordance with the present invention is the class known as the aminoglycoside class of antibiotics. This class of antibiotics has typically been administered intravenously, however, such delivery can sometimes have unwanted side effects, which may be systemic. Embodiments of the invention provide for the administration of antibiotics, such as aminoglycosides including amikacin by delivering them in aerosolized form into the breathing circuit of a patient on a ventilator. In this manner, amikacin can be used to treat pulmonary infection conditions that typically arise when patients are mechanically ventilated, and the amikacin, or other aminoglycoside or other antibiotic, can be delivered directly to the target of treatment, the pulmonary tract, avoiding side effects that may otherwise arise from intravenous administration. Further, because of the great cost of such drugs, far greater efficiency is achieved through this pulmonary delivery. As noted above with reference to FIG. 12C, delivery of aerosol during a beginning percentage of the inhalation phase of a breathing cycle may yield up between about 60% and about 80% efficiency, a significantly higher efficacy than continuous aerosolization, or aerosolization for an entire inhalation phase of an inhalation cycle.

Embodiments of the invention provide for conducting various regimes of aerosolization, depending on the situation. For example, in FIG. 14, a selection between a first, second and third regime is shown. A regime may be selected manually or automatically, for example, through the application of an algorithm that selects an operation program based on information that is either input or stored. For manual selection, a user may operate a mechanical switch to select a regime, or may enter such a selection into an electronic input device, such as a keyboard. Alternatively, the controller may automatically choose a regimen, as described above, by matching a drug code on a drug nebule with a library of drug-regimen combinations. (It should be noted that in FIGS. 14-17, schematic flow charts of operation sequence algorithms are depicted. Although items therein will be referred to as steps for ease of discussion, they refer more broadly herein to states of operations or modalities in which a system may exist or cycle through. Steps depicted in a rectangle are essentially states of operation, actions or modalities. Steps depicted in diamonds indicate either a selection or the continuance of the previous state of operation, action or modality until a predetermined condition is satisfied. Two successive diamonds refer to satisfaction of a first condition and of a second condition respectively, the second of which may be a subset of the first.)

In step 1400, a choice is made to follow a particular regime. In this case, regime I is a regime in which aerosol is generated continuously (step 1402). Regime II provides aerosol generation during the inhalation phase only (step 1404). In this case, in step 1406, aerosol generation is set to start at the start of the inhalation phase and, in step 1408, aerosol generation is set to stop when the inhalation phase stops. In step 1410, aerosol generation begins at the start of the inhalation phase. In step 1412, when the inhalation phase ends, aerosol generation stops (step 1414).

Regime III provides for inhalation during a predetermined percentage of the inhalation phase (step 1416). A predetermined percentage of an inhalation (or exhalation) phase may be based on a measured time from a discrete point in the ventilator cycle, such as the instantaneous commencement of inspiratory air generation by the ventilator. Alternatively, such predetermined percentage may be based on the time interval between successive discrete points in the ventilator, such as successive commencements of successive inhalation air generation by the ventilator. Alternatively, such percentages may be based upon air pressure in the ventilator circuit, or any other parameter. With respect to Regime III, in this case, in step 1418, a first predetermined point is set to correspond with the completion of a first predetermined percent of the inhalation. In step 1420, a second predetermined point is set to correspond to a second predetermined percent of inhalation percent being completed. For example, as described above, the first predetermined point may correspond to 20% of the inhalation phase being completed, and the second predetermined point may correspond to a point at which 70% of that same inhalation has taken place. In step 1422, aerosol generation begins at the first predetermined point in the inhalation phase. In step 1424, when the second predetermined point is reached, the controller carries out step 1414 and stops the aerosol generation.

Similarly, as noted above, other regimes may be followed, for example, in which aerosol generation begins during the inhalation phase and ends during the exhalation phase, or begins during exhalation and ends during that exhalation, or begins during exhalation and ends in the subsequent breath cycle, for example, at a predetermined point in the subsequent inhalation phase. Accordingly, turning to FIG. 15, a selection may be made, at step 1430, between regimes II (step 1432) and III (step 1434) as described above, and another regime, regime IV (steps 1436-1442), which is also available for selection. In regime IV, aerosol generation may begin at a first predetermined point (step 1436), and this first predetermined point may be after a predetermined percentage of the inhalation phase has taken place, or it may be a predetermined point after the inhalation phase has been completed. For example, this point may be a predetermined point after a predetermined percent of the exhalation phase has taken place, or may be a predetermined point prior to the start of the subsequent inhalation phase. Aerosol generation may stop during exhalation (regime IVa, step 1438), at the completion of exhalation (regime IVb, step 1440), or aerosol generation may continue into the next breath cycle (regime IVc, step 1442), and stop, for example, after a predetermined point during the subsequent inhalation phase.

Figure 16:
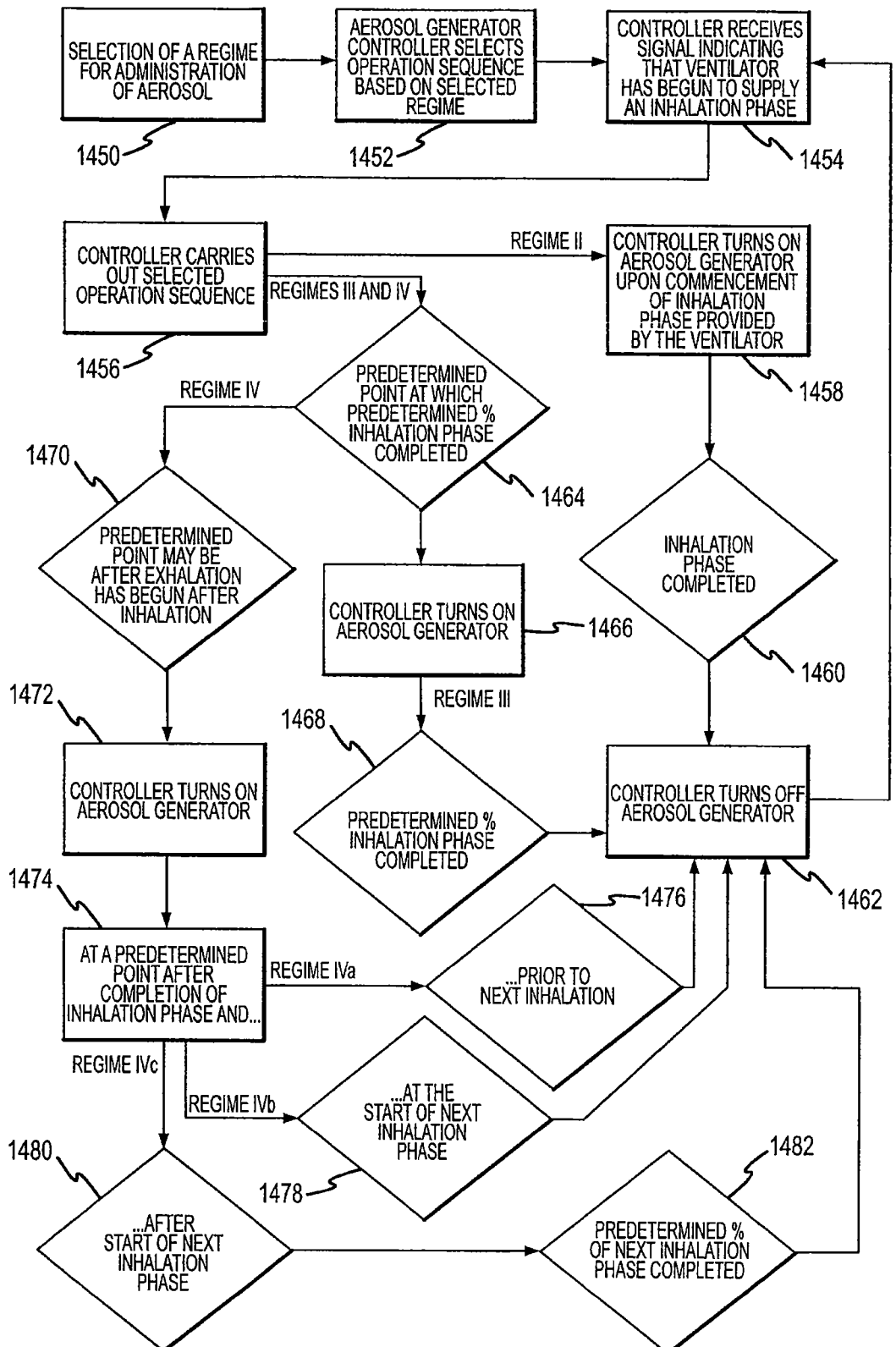
FIG. 16 is a further schematic representation of algorithms of operating sequences shown in FIG. 15, and in accordance with the present invention.

In this example, with the controller having a selection choice between operation sequences corresponding to regimes II, III and IV, schematic representation of the operation sequences are shown in FIG. 16. In step 1450, a regime is selected. In step 1452, the aerosol generator controller selects an operation sequence based on selected regime. In step 1454, the controller receives a signal indicating that ventilator has begun to supply an inhalation phase. The signal, as described above, may be a signal provided directly by the ventilator. Alternatively, the signal may be provided by a sensor, and such sensor may sense the commencement of an inhalation phase provided by the ventilator, as described above, by sensing a pressure change in the breathing circuit. In step 1456, the controller carries out selected operation sequence. In the case of regime II (step 1458), the controller turns on aerosol generator upon commencement of inhalation phase provided by the ventilator. The controller continues to operate the aerosol generator until a point at which the inhalation phase completed (step 1460). In step 1462, controller turns off aerosol generator.

In the case of regime III, the controller does not take any action to begin aerosol generation, until a predetermined point in the inhalation phase, corresponding to a percentage of the inhalation phase being completed (step 1464). In step 1466, at a predetermined point in the inhalation phase, the controller turns on aerosol generator. In step 1468, aerosol generation continues until a second predetermined point inhalation phase, corresponding to a second percentage point of completion of the inhalation phase. At this point, the controller carries out step 1462 and turns off aerosol generator. With respect to regime IV, aerosol generation begins after a predetermined point of completion of the inhalation phase (step 1464) and this point may be predetermined to occur after the inhalation phase has been completed and the exhalation phase has begun (step 1470). In step 1472, the controller turns the aerosol generator on to begin aerosolization. Variations can be made as to the point at which the aerosol generation is turned off. If it is desired that aerosol generation be completed before the completion of the exhalation phase (regime IVa), then aerosol generation may continue until a predetermined point prior to the subsequent inhalation (step 1476). Alternatively, it may be desirable to continue aerosolization until the end of exhalation, which may correspond to the point of commencement of the subsequent inhalation, as in regime IVb (step 1478). Alternatively, it may be desired to follow a regimen such as regime IVc, where aerosol generation continues through into the subsequent breath cycle (step 1480), until, for example, a predetermined percent of the subsequent inhalation phase has been completed (step 1482). In these regimes, aerosolization will continue until the satisfaction of these conditions (step 1476 for regime IVa, step 1478 for regime IVb or step 1482 for regime IVc), at which point the controller carries out step 1462 and stops the aerosol generator. The process may continue with the next signal indicating that the ventilator has begun to provide an inhalation phase, step 1454.

Further, the choice of which operating sequence to follow may rely at least in part on the identity of a drug to be administered, which information can be considered by the controller as described above. In addition, it should be appreciated that modifications may be made to these examples without departing from the present invention. For example, a system may be configured, or a method may be carried out, to be able to select more than three initial regimes to follow. For example, regimes I, II, III and IV as described above may be simultaneously selectable. Further, various steps may be altered; for example, some steps may not be discrete steps. Thus, step 1456 may not be a discrete step but rather the following of an operation sequence according to a selected regime. Similarly, the order of the steps may be changed, such as the controller may select an operating sequence (step 1452) after receiving a signal that the ventilator has commenced to provide an inhalation phase (step 1454). Steps may also be combined, such as, for example, in regime IV steps 1464 and 1470 may be combined as a single step, as these two steps represent successive criteria for the determining a single first predetermined point has been met. Likewise, step 1474 may be combined with steps 1476, 1478 or 1480, as step 1474 is the predicate for the condition test specified in each of the other successive tests, steps 1476, 1478 or 1480. The algorithm examples may be altered to form other operating sequences. For example, an operating sequence may call for the controller to start aerosol generation at the start of the inhalation cycle provided by the nebulizer, as in regime II, at step 1458, and turn off the aerosol generator at a point at which a predetermined percentage of the inhalation phase has been completed, as in regime III, step 1468 (and step 1462). In a similar manner, other criteria may be used to trigger the turning on or off of the aerosol generator. For example, as described above, the start of aerosolization may be triggered by the sensing of a particular pressure or change in pressure in the ventilator circuit, and may end by following the turning off sequence of regimes III (steps 1468 and 1462) or IV (steps 1474, 1476, 1478 or 1480 and 1482, followed by step 1462, as described above.

FIG. 17 is a schematic representation of an algorithm by which an operating sequence, for providing nebulized drug to a patient receiving air from a ventilator, may be chosen based on the combination of a plurality of independent sets of information, in this case, drug identity and a signal from the ventilator. In step 1700, a library of drug regimes is provided, the library based on various drugs that may be administered. In step 1702, the identity of a particular drug is provided to the system, and this may be provided, as described above, by a marker on a nebule containing the drug, the marker being read by the system. In step 1704, the controller looks up a regime from the library of stored regimes to select a regime based on the particular drug to be administered. In step 1706, the controller receives a signal from the ventilator. In step 1708, the controller then chooses an operation sequence based in part on the drug identity and drug regime and in part on the independent information provided by the signal from the ventilator. In step 1710, the controller carries out the operation sequence, which may be producing aerosol at a predetermined interval in the ventilation cycle based on the drug and the regime provided for the drug factored in with the inhalation cycle of the ventilator. These descriptions are illustrative, and accordingly, the order of the steps may be altered, and other variations, additions and modifications, as described above, may be made still in accordance with the present invention.

The phasic delivery methods outlined above may also be practiced with additional systems such as continuous positive airway pressure ("CPAP") systems, such as the ones described in U.S. patent application Ser. No. 10/828,765, filed Apr. 20, 2004, U.S. patent application Ser. No. 10/883,115, filed Jun. 30, 2004, now U.S. Pat. No. 7,290,541, and U.S. patent application Ser. No. 10/957,321, filed Sep. 9, 2004, now U.S. Pat. No. 7,267,121, where the entire continents of all the applications are herein incorporated by reference for all purposes.

EXPERIMENTAL

Delivery efficacy tests were conducted with an on-ventilator PDDS aerosolizing an aqueous solution of amikacin sulfate. The PDDS ventilator circuit configuration was similar to the one shown and described in FIG. 2 above. A 400 mg dose of the amikacin was run through the PDDS. The PDDS was configured to deliver the aerosolized medicament by a phasic delivery regime similar to the one shown in FIG. 12C. The medicament dose was delivered over the course of about 50 to about 60 minutes.

Table 2 presents efficiency data for the delivery of aerosolized medicament to through systems according to embodiments of the invention. In the experimental setup, aerosolized droplets deposited on an inspiratory filter placed at a patient end interface are weighed and compared to the total weight of the dose of medicament that was aerosolized. The percentage of a dose deposited on the inspiratory filter represents the fraction of the total aerosolized dose that would be inhaled by a patient, and thus quantifies the efficiency of the system.

TABLE 2

Percent of Dose Deposited on Inspiratory Filter

| Run No. | Percent Deposited on Filter | Mean | Standard Deviation | % RSD |
| --- | --- | --- | --- | --- |
| 1 | 69% | 71% | 0.04 | 6% |
| 2 | 75% | | | |
| 3 | 75% | | | |
| 4 | 77% | | | |
| 5 | 69% | | | |
| 6 | 66% | | | |
| 7 | 68% | | | |

Table 2 shows the efficiencies of 7 runs for a system according to an embodiment of the invention had a mean efficiency of 71%±6%. This efficiency level is well above conventional systems for the delivery of aerosolized medicaments, where the efficiency levels are typically 10% or less.

Having described several embodiments, it will be recognized by those of skill in the art that various modifications, alternative constructions, and equivalents may be used without departing from the spirit of the invention. Additionally, a number of well known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the electrode" includes reference to one or more electrodes and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, acts, or groups.

What is claimed is:

1. A system for intermittent delivery of an aerosolized medicament, the system comprising:
   an aerosol generator that aerosolizes a medicament;
   a controller, that:
   receives physiological characteristic information about a patient;
   receives information about the type of medicament being delivered;
   stores at least some of the physiological characteristic information;
   selects a mode of operation from a plurality of modes based at least in part on the type of medicament being delivered, each mode prescribing a respective first condition for determining when within the patient's breathing cycle aerosolization is started and a respective second condition for determining when within the patient's breathing cycle aerosolization is stopped; and
   controls the aerosol generator based at least in part on the stored physiological characteristic information and according to the selected mode of operation; and
   a conduit through which the aerosolized medicament is supplied to the patient's airway.

2. The system of claim 1, wherein the physiological characteristic information comprises data representative of breathing.

3. The system of claim 1, wherein the aerosol generator comprises:
   an aerosolization element defining a plurality of apertures; and
   a vibratory element that vibrates the aerosolization element.

4. The system of claim 3, wherein the aerosolization element has a first side and a second side, and wherein when the aerosolization element is vibrated, a liquid medicament at the first side moves through the apertures and is ejected as aerosolized medicament from the second side.

5. The system of claim 1, wherein the physiological characteristic information comprises breathing characteristic information, and wherein the controller activates the aerosol generator once a threshold level of inhalation has been achieved.

6. The system of claim 1, wherein the controller further:
   stores at least one aerosol generator operation program; and controls the aerosol generator based at least in part on the aerosol generator operation program.

7. The system of claim 6, wherein the aerosol generator operation program comprises at least two instructions selected from a group consisting of:
   (i) activate the aerosol generator at a predetermined point in an inhalation phase of the patient, and deactivate the aerosol generator at a predetermined point in the inhalation phase of the patient;
   (ii) activate the aerosol generator at a predetermined point in the inhalation phase of the patient, and deactivate the aerosol generator at a predetermined point in an exhalation phase of the patient;
   (iii) activate the aerosol generator at a predetermined point in the exhalation phase of the patient, and deactivate the aerosol generator at a predetermined point in the exhalation phase of the patient; and
   (iv) activate the aerosol generator at a predetermined point in the exhalation phase of the patient, and deactivate the aerosol generator at a predetermined point in the inhalation phase of the patient.

8. The system of claim 6, wherein the conduit comprises a ventilator circuit, and wherein:
   the physiological characteristic information is received from the ventilator circuit; and
   the aerosol generator operation program comprises at least two instructions selected from a group consisting of:
   (i) activate the aerosol generator at a predetermined point in an output phase of the ventilator circuit, and deactivate the aerosol generator at a predetermined point in the output phase of the ventilator circuit;
   (ii) activate the aerosol generator at a predetermined point in the output phase of the ventilator circuit, and deactivate the aerosol generator at a predetermined point in a non-output phase of the ventilator circuit;
   (iii) activate the aerosol generator at a predetermined point in the non-output phase of the ventilator circuit, and deactivate the aerosol generator at a predetermined point in the non-output phase of the ventilator circuit; and
   (iv) activate the aerosol generator at a predetermined point in the non-output phase of the ventilator circuit, and deactivate the aerosol generator at a predetermined point in the output phase of the ventilator circuit.

9. The system of claim 1, wherein the system further comprises a sensor that monitors and transmits physiological characteristic information.

10. The system of claim 9, wherein the sensor comprises a pressure sensor that senses pressure changes in the conduit.

11. The system of claim 1, wherein the conduit comprises a ventilator circuit.

12. The system of claim 11, wherein the controller activates the aerosol generator once a threshold level of respiratory gas is supplied by the ventilator circuit.

13. The system of claim 1, wherein:
   when the information about the type of medicament delivered indicates that the type of medicament is a steroid, the controller controls the aerosol generator such that the medicament is delivered towards the end of an inhalation phase of a breath; and
   when the information about the type of medicament delivered indicates that the type of medicament is an antibiotic, the controller controls the aerosol generator such that aerosol generation occurs at the beginning of a breath and stops after a predetermined percentage of inhalation has occurred.

* * * * *